US010167463B2

(12) United States Patent
Dekker et al.

(10) Patent No.: US 10,167,463 B2
(45) Date of Patent: Jan. 1, 2019

(54) MODIFIED CHYMOSIN POLYPEPTIDES

(71) Applicant: DSM IP ASSETS B.V., Heerlen (NL)

(72) Inventors: Petrus Jacobus Theodorus Dekker, Echt (NL); Rene Marcel De Jong, Echt (NL); Michael Dennis Tabeling, Echt (NL); Cornelis Marinus Muijlwijk, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 413 days.

(21) Appl. No.: 14/397,865

(22) PCT Filed: May 3, 2013

(86) PCT No.: PCT/EP2013/059317
§ 371 (c)(1),
(2) Date: Oct. 30, 2014

(87) PCT Pub. No.: WO2013/164481
PCT Pub. Date: Nov. 7, 2013

(65) Prior Publication Data
US 2015/0140169 A1     May 21, 2015

Related U.S. Application Data

(60) Provisional application No. 61/642,095, filed on May 3, 2012, provisional application No. 61/745,063, filed on Dec. 21, 2012.

(30) Foreign Application Priority Data

May 3, 2012   (EP) .................................... 12166673
Dec. 21, 2012 (EP) .................................... 12199178
Dec. 21, 2012 (EP) .................................... 12199277

(51) Int. Cl.
  *C12N 9/64*    (2006.01)
  *A23C 19/032*  (2006.01)
  *A23C 19/068*  (2006.01)
  *A23C 19/072*  (2006.01)

(52) U.S. Cl.
  CPC .......... *C12N 9/6483* (2013.01); *A23C 19/032* (2013.01); *A23C 19/0326* (2013.01); *A23C 19/0684* (2013.01); *A23C 19/072* (2013.01); *C12Y 304/23004* (2013.01); *A23C 2220/202* (2013.01); *A23C 2250/15* (2013.01)

(58) Field of Classification Search
  None
  See application file for complete search history.

(56) References Cited

FOREIGN PATENT DOCUMENTS

WO   2008098973 A1   8/2008

OTHER PUBLICATIONS

D. Quinn et al. "Modifying the Substrate Specificity of Chymosin", Biochemical Society Transactions 19:267S (1991).*
International Search Report from corresponding PCT/EP2013/059317, dated Jun. 26, 2013.
Suzuki et al., "Alteration of catalytic properties of chymosin by site-directed mutagenesis", XP000009488, 6123 Protein Engineering, vol. 2, No. 7, pp. 563-569, May 1989, Eynsham, Oxford, GB.
Suzuki et al., Site-directed mutagensis reveals functional contribution of Thr218, Lys220 and Asp304 in chymosin, Department of Agriculture Chemistry, Faculty of Agriculture, The University of Tokyo, Tokyo, Japan, Protein Engineering, vol. 4, No. 1, pp. 69-71, 1990.
Chitpinityol et al., "Chymosin and aspartic proteinases", XP-002685254, Food Chemistry, vol. 61, No. 4, pp. 395-418, 1998.
Chitpinityol et al., "Site-specific mutations of calf chymosin B which influence milk-clotting activity", XP-002685255, Food Chemistry, vol. 62, No. 2, pp. 133-139, 1998.
McSweeney et al., "Proteolytic specificity of chymosin on bovine as1-casein", Journal of Dairy Research (1993) 60 pp. 401-412, Printed in Great Britain, XP009099544.
Carles et al., "Kinetics of the action of chymosin (rennin) on a peptide bond of bovine as1-casein, Comparison of the behaviour of this substrate with that of B-and Ko-caseins", vol. 185, No. 2, FEBS Letters, 2638, Jun. 1985, pp. 282-286, XP025603894.
Bansal et al., "Suitability of recombinant camel (*Camelus dromedarius*) chymosin as a coagulant for Cheddar cheese", International Dairy Journal 19 (2009) 510-517, Elsevier, XP026152366.
Moller et al, "Camel and Bovine Chymosin Hydrolysis of Bovine as1-and B-Caseins Studied by Comparative Peptide Mapping", Journal of Agricultural and Food Chemistry, Faculty of Science, University of Copenhagen, Frederiksberg C, Denmark, XP055063786, ACS Publications, 2012 American Chemical Society, pp. 11421-11432.
Kappeler, Stefan R. et al., "Characterization of recombinant camel chymosin reveals superior properties for the coagulation of bovine and camel milk", Biochemical and Biophysical Research Communications, 2006, pp. 647-654, vol. 342.

\* cited by examiner

*Primary Examiner* — Rebecca E Prouty
(74) *Attorney, Agent, or Firm* — McBee Moore Woodward & Vanik IP, LLC; Susan McBee; Chester Moore

(57) ABSTRACT

The invention relates to a polypeptide having chymosin activity which: a. is capable of hydrolyzing bovine alpha s1-casein at position F23F24 so as to form αs1-I CN (f24-199) more rapidly than camel chymosin; and b. has a C/P ratio higher than the C/P ratio of bovine chymosin.

16 Claims, 2 Drawing Sheets

Specification includes a Sequence Listing.

MODIFIED CHYMOSIN POLYPEPTIDES

CROSS REFERENCE TO RELATED APPLICATIONS

This application is a § 371 National Stage Application of PCT/EP2013/059317, filed May 3, 2013, which claims priority to EP 12166673.9, filed May 3, 2012, to U.S. 61/642,095, filed May 3, 2012, to EP 12199277.0, filed Dec. 21, 2012, to EP 12199178.0, filed Dec. 21, 2012 and to U.S. 61/745,063, filed Dec. 21, 2012.

BACKGROUND

Field of the Invention

The invention relates to a polypeptide having modified chymosin activity. The invention also relates to a nucleic acid sequence encoding such a polypeptide, to a recombinant expression vector a said nucleic acid construct and to a recombinant host cell comprising a said expression vector. Further, the invention relates to a method for producing a modified chymosin polypeptide via use of such a host cell. Also, the invention relates to a method of producing a modified chymosin polypeptide. The invention further relates to a composition comprising a modified chymosin, to use of such a modified chymosin or modified chymosin-containing composition in the preparation of a cheese, to a process for the production of a cheese and to the resulting cheese.

Description of Related Art

A large part of global cheese production is used as grated or sliced cheese for use on pizza, cheese burgers and other convenience foods. Cheese used for this purpose is general young where little ripening has occurred. Cheese types used for this application may be Mozzarella, Monterey Jack or processed cheese or other types of cheeses that are industrially sliced or shredded and consumed as young cheese.

Shredding allows for faster melting of cheese, as compared with other methods of size reduction such as slicing and cubing. Shreddability is a broad term that encompasses many characteristics of shredded cheese. It can take into account the ease with which the block of cheese is processed through the shredding machine, the geometry and integrity of the cheese shreds (length and thickness of cut, ragged or clean edges), the propensity of shreds to remain free flowing or mat together after shredding, and the propensity of shredded particles to shatter into fines either during or after shredding. If cheese is soft, pasty, or wet, the shredder can become clogged with cheese. The shredded cheese may also produce shreds with ragged edges, many fines, gummy balls of cheese, and excessive matting of the cheese shreds. In contrast, if the cheese is too firm and dry, the resulting shreds are typically shattered into smaller particles and fines.

Ideally, cheese shreds should be cut uniformly and precisely, which allows the cheese to melt evenly and easily. Considerable importance is placed on the integrity of cheese shreds with regard to uniform size and shape, so it is crucial that the shreds retain these characteristics during handling, distribution, and storage. Considerable emphasis is also put on the amount of fines produced during shredding. Production of fines causes waste that cheese processors would like to avoid.

Shredding (shredding) and slicing of cheese is problematic when the cheese is too young because of severe production losses. In Mozzarella cheese, for a week or two post-manufacture some free serum can be observed when the cheese is cut ("watering-off"). The reduction in the amount of expressible serum in Mozzarella cheese as it ages is often ascribed to an increase in protein hydration as water is absorbed into the matrix. As the cheese ages the watering-off decreases and after ~two weeks only very little serum is expressed upon cutting. Therefore, shredding or slicing before this age will lead to severe yield losses.

Also cheddar cheese requires about four weeks of ripening before shredding, adding refrigerated storage and handling costs to the product. Key attributes improved by this ripening period include the reduction of crumbs (fines) and improvements in surface smoothness, shred mean length, and size uniformity. In very young cheddar the cheese matrix is still too hard and brittle, and the fusion of curd particles ("knitting") is not complete. After a few weeks of storage the cheese matrix softens and the cheese can be used for shredding and/or slicing.

On the other hand, prolonged ripening often leads to softening of the texture of Mozzarella. Extensive ripening gives soft and gummy body and has a negative effect on the industrial shredding or slicing and leads to productivity losses due to clumping of shreds and adhesion of cheese to the shredding equipment surfaces. Also in semi-hard cheeses like Cheddar, ripening leads to increased adhesiveness and stickiness. Therefore the maximum storage time of these cheese types before industrial processing by shredding or slicing is often limited.

From this it becomes clear that efficient shredding and/or slicing of cheese at an industrial scale is only possible within a specific time frame where the cheese has the required texture. The exact time window that may be used for this depends very much on the cheese type and storage conditions.

For the industry it is relevant that this time window is as broad as possible; i.e. shredding/slicing may commence as soon as possible and can still be performed on cheeses that have been stored for a longer time.

It is generally believed that ripening of cheese is initiated by the coagulant that is captured in the curd during cheese making. Coagulants currently used in industry have besides their activity on kappa-casein during the milk coagulation process, also low activity on the other caseins that form part of the cheese matrix. It is thought that this proteolytic activity is involved in both the early knitting of Cheddar particles and reduction of watering-off in Mozzarella cheese, but also the further ripening and softening of the cheese matrix upon prolonged storage. To prevent excessive ripening the general proteolytic activity of the coagulant should be low compared to the milk-clotting activity.

This property of a coagulant can be quantified by measuring the C/P ratio; the clotting activity divided by the general proteolytic activity.

The ideal coagulant for the production of young cheese for industrial use will be one that leads not only to a prolonged storage, but also to fast processibility early in the ripening, without extensive storage. However, since fast processibility requires high proteolytic activity but prolonged storage requires low proteolytic activity on the casein matrix, it is not clear how these two properties might be combined in a single coagulant.

SUMMARY

The invention is based on the identification of a coagulant which performs the first cut in alpha s1-casein efficiently, forming alpha s1-I-casein, but has low activity for further casein digestion. In view of this combination of properties, the coagulant of the invention is a superior coagulant for the production of, in particular, young industrial cheeses.

The coagulant of the invention leads to a fast early development in ripening due to the rapid first cut in alpha s1-casein, but also leads to the possibility of prolonged storage of the cheese due to the high C/P value.

Such a coagulant has not been described before since all existing coagulants either have fast ripening due to the high proteolytic activity, or have possibilities for increased storage due to low proteolytic activity. These properties have not previously been combined together in one enzyme.

According to the invention, there is thus provided a polypeptide having chymosin activity which:
  a. is capable of hydrolysing bovine alpha s1-casein at position F23F24 so as to form αs1-I CN (f24-199) more rapidly than camel chymosin; and
  b. has a C/P ratio higher than the C/P ratio of bovine chymosin.

The invention further provides a polypeptide having chymosin activity and having an amino acid sequence which;
  a. when aligned with the chymosin comprising the sequence set out in SEQ ID NO: 2, comprises at least one substitution of an amino acid residue corresponding to amino acid 51 and/or 221; and/or
  b. when aligned with SEQ ID NO: 4 comprises at least one substitution of an amino acid residue located in the S2 binding pocket, for example at a position corresponding to position 223.

The invention also provides:
a nucleic acid encoding a polypeptide of the invention;
a nucleic acid construct comprising a nucleic acid sequence of the invention operably linked to one or more control sequences capable of directing the expression of a chymosin in a suitable expression host;
a recombinant expression vector comprising a nucleic acid construct of the invention;
a recombinant host cell comprising a expression vector of the invention;
a method for producing a chymosin comprising cultivating a host cell of the invention under conditions conducive to production of the chymosin and recovering the chymosin;
a method of producing a chymosin polypeptide variant, which method comprises:
  a) selecting a polypeptide having chymosin activity;
  b) substituting at least one amino acid residue corresponding to:
    position 51 or 221 as defined with reference to SEQ ID NO: 2; and/or a position within the S2 binding pocket as defined with reference to SEQ ID NO: 4;
  c) optionally substituting one or more further amino acids as defined in b);
  d) preparing the variant resulting from steps a)-c);
  e) determining a property of the variant; and
  f) selecting a variant having an altered property in comparison a reference polypeptide having chymosin activity, thereby to produce an chymosin polypeptide variant;
a composition comprising a polypeptide of the invention or obtainable by a method of the invention for producing a chymosin;
use of a polypeptide of the invention or of a composition of the invention in the preparation of a cheese;
a process for the production of a cheese, which method comprises comprising adding a milk clotting effective amount of a polypeptide of the invention or of a composition of the invention to milk and carrying out appropriate further cheese manufacturing steps; and
a cheese obtainable by the process of the invention or by use according to the invention.

BRIEF DESCRIPTION OF THE SEQUENCE LISTING

Figure 1:
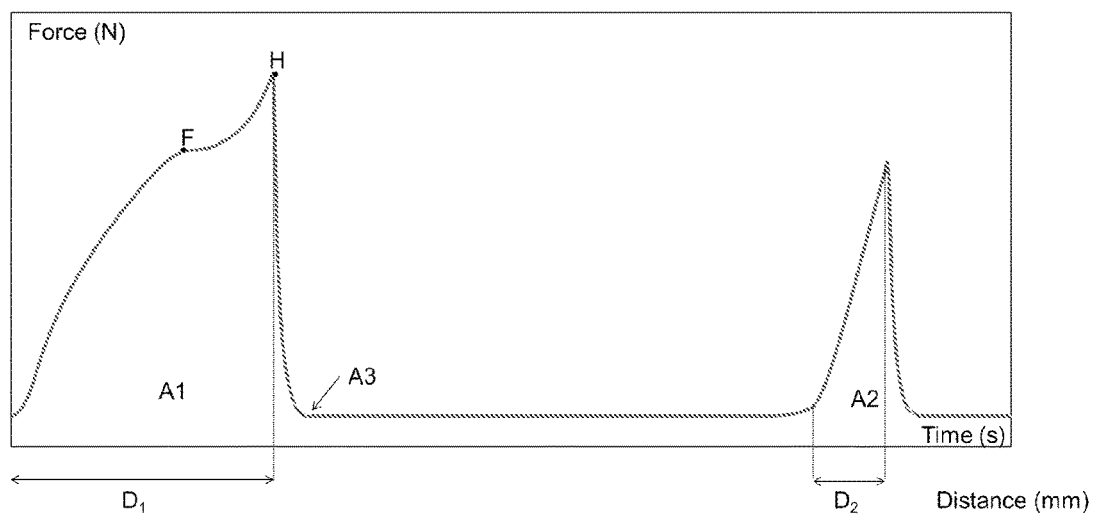
FIG. 1 sets out a typical TPA curve during a double bite compression test.

SEQ ID NO: 1 sets out the nucleic acid sequence of the wild type pro-chymosin B gene sequence from *Bos taurus* with codon adaptation for expression in *K. lactis* and with linkers to allow cloning into pKLAC1.

SEQ ID NO: 2 sets out the amino acid sequence of the mature chymosin B sequence from *Bos taurus*.

SEQ ID NO: 3 sets out the nucleic acid sequence of the pro-chymosin sequence from *Camelus dromedarius* with codon adaptation for expression in *K. lactis*.

SEQ ID NO: 4 sets out the amino acid sequence of the mature chymosin sequence from *Camelus dromedarius*.

SEQ ID NO: 5 sets out the amino acid sequence of alpha-s1 casein from *Bos Taurus*.

DETAILED DESCRIPTION OF A PREFERRED EMBODIMENT

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to variant coagulants, in particular variant chymosin polypeptides. A variant of the invention will typically retain chymosin activity. That is to say, a variant of the invention will typically be capable of aspartic protease activity. A variant of the invention is one which is typically capable of clotting milk and which may be used in the preparation of a food product, such as a cheese.

A variant of the invention will typically exhibit improved properties in comparison with the reference chymosin polypeptide from which it is derived, typically a wild type reference chymosin. Such an improved property will typically be one which is relevant if the variant were to be used as set out below, for example in a method for preparing a cheese.

Herein, "chymosin" typically indicates an aspartic protease, group 3.4.23.4 according to the Enzyme Nomenclature, 1992 of the International Union of Biochemistry and Molecular Biology, IUBMB. Chymosin is naturally produced by gastric chief cells in juvenile mammals. Chymosin is the main enzymatic component in rennet. Calf rennet is obtained of the lining of the abomasum (the fourth and final, chamber of the stomach) of young, unweaned calves.

Prochymosin is in context of the present invention to be understood as the precursor or proenzyme of chymosin. Prochymosin appears to possess a leader sequence (pro-part) on the N-terminal side of chymosin and said leader sequence is believed to be cleaved off during activation of the prochymosin. Furthermore in this context, preprochymosin consists of prochymosin to which is added on the N-terminal end of prochymosin a hydrophobic leader sequence. This leader sequence, also called secretion signal or prepart, is cleaved off when the protein is secreted. Chymosin is in the cell initially synthesised as preprochymosin (Harris et al., Nucleic acid Research 1982, April 10, 2177-2187 Molecular cloning and nucleotide sequence of cDNA coding for calf preprochymosin).

The invention relates to a new variant coagulant, i.e. variant of a chymosin, that performs the first cut in alpha s1-casein efficiently, forming alpha s1-I-casein, but has low activity for further casein digestion, and is thus a superior coagulant for the production of young industrial cheeses.

Such a chymosin leads to a fast early development in the ripening due to the rapid first cut in alpha s1-casein, but also leads to the possibility of prolonged storage of the cheese due to the high C/P value. These properties are demonstrated independently by the wild type bovine and camel chymosins respectively. Accordingly, variants of the invention may be a modified bovine chymosin into which is engineered a higher C/P value or a modified camel chymosin in which is engineered the ability to more rapidly carry out the first cut in alpha s1-casein. Accordingly, a chymosin variant of the invention is typically not a wild-type sequence.

This type of chymosin has not previously been described since all existing coagulants either have fast ripening due to high proteolytic activity, or have the possibility for use in prolonged storage due to low proteolytic activity. However, these two properties have not previously been combined in one enzyme, whereas the invention now provides such an enzyme.

Herein is also described how to recognize chymosins with these combined properties, methods for screening for such coagulants, and methods for engineering these properties into an existing coagulant.

According to the invention, there is thus provided a polypeptide having chymosin activity which:
  a. is capable of hydrolysing bovine alpha s1-casein at position F23F24 so as to form αs1-I CN (f24-199) more rapidly than camel chymosin; and
  b. has a C/P ratio higher than the C/P ratio of bovine chymosin.

In this context, bovine chymosin may refer to any wild type bovine chymosin, such as the mature bovine chymosin sequence set out in SEQ ID NO: 2 and camel chymosin may refer to any mature camel chymosin, such as the mature camel chymosin sequence set out in SEQ ID NO: 4.

In particular, such a polypeptide of the invention may be one wherein the hydrolysis of bovine alpha s1-casein (αs1 CN) at position F23F24 forming αs1-I CN (f24-199) is at least about 1.1, at least about 1.2, at least about 1.25, for example at least about 1.5, such as at least about 2.0, for example at least about 2.5 times more rapid than camel chymosin.

A sequence of bovine alpha s1-casein is set out in SEQ ID NO: 5 (without the 15 amino acid signal peptide) and the sequence is also set out as UNIPROT Accession P02662.

Position F23F24 refers to the two phenylalanine residues at positions 23 and 24 in SEQ ID NO: 5. There are several isogenes for this protein with slightly different amino acid sequences, but the skilled person will be able to identify the amino acids corresponding to F23 and F24 in SEQ ID NO: 5.

Alpha s1-I casein (αs1-I CN (f24-199)) is a hydrolysis product of one of the major proteins (αs1-CN) in milk. αs1-I CN (f24-199) is the first fragment of αs1-CN to be produced by the action of coagulant during ripening of cheese where chymosin has digested the F23F24 bond of αs1-CN.

Hydrolysis of the F23F24 bond in alpha-s1 casein can be measured in different ways. Speed or rate of hydrolysis may be compared, for example, in terms of amount of enzyme (for example in terms of mg protein) or in terms of an equivalent amount of IMCUs. A higher rate of hydrolysis than camel chymosin is indicative of a polypeptide of the invention that is capable of hydrolysing bovine alpha s1-casein at position F23F24 so as to form αs1-I CN (f24-199) more rapidly than camel chymosin.

As described herein (see the Examples—Materials and Methods section and Example 8 and 9 in particular), alpha-casein can be used as substrate and incubated with specific chymosin variants under defined conditions. Afterwards the hydrolysis can be analyzed using PAGE, staining of the protein bands, identification of the different bands, and scanning and densitometric analysis of the different hydrolysis products. Such an analytical method to quantify alpha-s1 casein and alpha-s1 I casein (αs1-CN(f24-199)), obtained with different coagulants, has been described previously in literature (see e.g. Bansal et al (2009) International Dairy Journal 19, 510-517). A comparable densitometric analysis to quantify alpha-s1 casein and its degradation products is described in Examples 8 and 9.

Alternatively, hydrolysis of the F23F24 bond in alpha-s1 casein and formation of the hydrolysis products can be followed using RP-HPLC and quantified using a described technique (Caries and Dumas (1985) FEBS Letters 185(2), 282-286). The rate of the appearance of the alpha-s1 I fragment and the disappearance of the intact alpha-s1 casein can be conveniently monitored using this technique. It will be clear to a person skilled in the art that such RP-HPLC can also be used to quantify alpha-s1 casein and its degradation products.

A method to quantify the rate of formation of this first cut in αs1-CN is also described in public literature (Møller et al (2012) J. Agric. Food Chem. 60, 11421-11432).

Any of the above methods may be used to determine the rate at which a chymosin polypeptide is capable of hydrolysing bovine alpha s1-casein at position F23F24 so as to form αs1-I CN (f24-199).

Rate of hydrolysis can be expressed as the ratio of αs1-I CN to αs1 CN formed upon incubation of alpha casein with chymosin as described in the Examples—Materials and Methods section and Example 8 and 9 in particular.

Accordingly, a chymosin variant of the invention may be capable of hydrolysing bovine alpha s1-casein at position F23F24 so as to form αs1-I CN (f24-199) more rapidly than camel chymosin, can be defined as a chymosin variant that produces a ratio of αs1-I CN to αs1 CN of higher than about 0.5 when the incubation with alpha casein is performed for 6 hours at 11° C. or a ratio of αs1-I CN to αs1 CN of higher than about 1.5 when the incubation with alpha casein is performed for 24 hours at 11° C.

Accordingly, a chymosin variant capable may be capable of hydrolysing bovine alpha s1-casein at position F23F24 so as to form αs1-I CN (f24-199) more rapidly than camel chymosin, can be defined as a chymosin variant that produces a ratio of αs1-I CN to αs1 CN of higher than about 0.5 when the incubation with alpha casein is performed for 6 hours at 11° C. and a ratio of αs1-I CN to αs1 CN of higher than about 1.5 when the incubation with alpha casein is performed for 24 hours at 11° C.

In particular, a polypeptide of the invention may be one wherein the C/P ratio is about 2, for example about 5, for example about 10, such as about 10 times higher than the C/P ratio of bovine chymosin.

The term C/P refers to the clotting activity divided by the proteolytic activity of a specific enzyme sample. The C/P is a measurement of the specificity of the coagulant. The methods to measure both activities and calculate the C/P is described herein (see the Examples). The method to measure the clotting activity (C) will quantify the efficiency of the enzyme sample to hydrolyse kappa-casein (k-CN) at a specific position (F105M106). The proteolytic activity (P) will quantify the ability of the coagulant to hydrolyse casein into small (TCA-soluble) peptide fragments and amino acids.

Herein, the term "IMCU" is understood International Milk Clotting Units. One IMCU equals about 0.126 nmol of bovine chymosin B (e.g. Maxiren or CHY-MAX). The strength of a milk clotting enzyme (such as chymosin enzyme present in a composition of the present invention) is determined as the milk clotting activity (IMCU per ml or per gram). Following the addition of diluted coagulant to a standard milk substrate, the milk will flocculate. The milk clotting time is the time period from addition of the coagulant until formation of visible flocks or flakes in the milk substrate. The strength of a coagulant sample is found by comparing the milk clotting time for the sample to that of a reference standard, a normal. This is expressed in IDF standard 157A:1997 which gives the IMCU definition: The total milk-clotting activity of the first batch of calf chymosin reference standard powder has once and for all been set at 1000 International Milk-Clotting Units per gram (IMCU/g). Further preparations of reference standards will be set relative to the previous reference. IMCU principle: Determination of the time needed for visible flocculation of renneted standard milk substrate with 0.05% calcium chloride, pH6.5. IMCU/ml of a sample is determined by comparison of the clotting time to that of a standard having known milk clotting activity and having the same enzyme composition of the sample.

A chymosin variant of the invention may typically have a high specific milk clotting activity (C) and a low general, i.e. non-specific, proteolytic activity (P) with regard to milk proteins. Accordingly, the C/P ratio should preferably be as high as possible, as a relatively high P-value, during the cheese manufacturing process and during maturation of the cheese will lead to the formation of low molecular peptides and free amino acids, which in turn may confer to the finished cheese an undesirable bitter taste and also result in a loss of cheese yield. C/P ratio may be expressed as a relative C/P ratio, for example in relation to a chymosin such as the bovine chymosin of SEQ ID NO: 2.

The invention also provides a polypeptide having chymosin activity and having an amino acid sequence which;
  a. when aligned with the chymosin comprising the sequence set out in SEQ ID NO: 2, comprises at least one substitution of an amino acid residue corresponding to amino acid 51 and/or 221; and/or
  b. when aligned with SEQ ID NO: 4 comprises at least one substitution of an amino acid residue located in the S2 binding pocket, for example at a position corresponding to amino acid 223.

Such a protein will typically be: capable of hydrolysing bovine alpha s1-casein at position F23F24 so as to form αs1-I CN (f24-199) more rapidly than camel chymosin; and have a C/P ratio higher than the C/P ratio of bovine chymosin.

Thus, at a position corresponding to amino acid 51 and/or 221 as defined with reference to SEQ ID NO: 2, a different amino acid may be present than is present at amino acid 51 and/or 221 in SEQ ID NO: 2. Thus, at a position corresponding to an amino acid in the S2 binding pocket as defined with reference to SEQ ID NO: 4, a different amino acid may be present than is present at that position within the S2 binding pocket in SEQ ID NO: 4.

Typically, a polypeptide in the invention is a polypeptide having at least about 65% homology with SEQ ID NO: 2 or SEQ ID NO: 4, for example at least about 70% homology with SEQ ID NO: 2 or SEQ ID NO: 4, such a least about 75% homology with SEQ ID NO: 2 or SEQ ID NO: 4, such as at least about 80% homology with SEQ ID NO: 2 or SEQ ID NO: 4, for example at least about 85%, at least about 90%, at least about 95%, at least about 98% or at least about 99% homology with SEQ ID NO: 2 or SEQ ID NO: 4.

Increased early development of cheese curd is related to the affinity of a specific region of alpha s1-casein to the different binding pockets in the peptide-binding groove of the coagulant. Accordingly, herein are described amino acids in the S2 binding pocket (Schechter en Berger (1967) Biochem. Biophys. Res. Commun. 27, 157-162) relevant for this affinity and this affinity may be modulated by altering amino acids in this pocket in order to increase the rate of hydrolysis of bovine alpha s1-casein at position F23F24 so as to form αs1-I CN (f24-199).

For example, introduction of a different amino acid side chain at position V223, as defined with reference to the sequence of the bovine chymosin, leads to a reduced first cut in alpha s1-casein. However, any chymosin with an amino acid change at the corresponding position, and other neighboring positions in the S2 binding pocket may lead to an altered affinity of the alpha s1-casein for the chymosin and a change in the kinetics of the first cut in alpha s1-casein.

Amino acid changes at the positions that are part of the S2 binding pocket are, most notably, T219, F223, Q288, D290, L295 and I297 in camel chymosin or amino acids at equivalent positions in other mammalian chymosins (e.g. T219, V223, Q288, E290, K295 and I297 in bovine chymosin), may also modulate the affinity of the alpha s1-casein for the chymosin, and thus alter the kinetics of the first cut in alpha s1 casein.

Accordingly, preferred variant chymosin polypeptides of the invention may comprise the sequence set out in SEQ ID NO: 4 carrying one of the following mutations:
F223C, F223D, F223E, F223L, F223M, F223N, F223Q, F223V, F223Y, F223I
Q288G, Q288H, Q288N, Q288R, Q288S
D290A, D290G, D290L, D290M, D290Q, D290S, D290T
L295F, L295I, L295K, L295M, L295R, L295T, L295Y, L295W
I297T, I297V Combinations of such mutations at different positions may be used.

For a person skilled in the art it will be clear how to use, for example saturation mutagenesis or site-directed mutagenesis, to change the amino acid positions in the S2 pocket in bovine chymosin or the equivalent amino acids in chymosins originating from other mammals, for example a camel chymosin, to obtain a chymosin with altered digestion kinetics of the first cut in alpha s1-casein, and thereby will lead to a change in the textural characteristics of a cheese made with such a variant.

Amino acid changes relevant for a higher C/P value of the bovine coagulant are also described herein. We describe that changes in amino acids A51 and K221 within the bovine chymosin amino acid sequence are important for an increased C/P. Introduction of these changes in a coagulant of choice will lead to a higher C/P value and therefore increased storage stability of the cheese made with such coagulant.

Other positions that may be substituted (as defined with reference to the bovine sequence of SEQ ID NO: 2) are 48, 50, 61, 62, 109, 117, 126, 135, 144, 160, 161, 201, 202, 203, 221, 240, 242, 244, 254, 267, 280, 292 or 295. One or more of these positions may be changed so that it is different from the amino acid at that position as defined with reference to the bovine sequence of SEQ ID NO: 2.

Preferred variant chymosin polypeptides of the invention may comprise the sequence set out in SEQ ID NO: 2 carrying one of the following mutations or combinations of mutations:

A51V;
K221L;
K221M;
K221V;
V223Q;
A51V and K221V;
A51V and K221M;
A51V, K221V, S135T, A126G, S273Y and Q240E;
A51I and K221T; or
A51V, K221V, N50D, N144H, N160D, S201D, Q242E, M267E and Q280E According to the invention, two properties are combined that permits, for example, the construction of a calf chymosin variant having higher C/P value useful or the construction of a camel chymosin variant having capable of more rapidly hydrolysing bovine alpha s1-casein at position F23F24 so as to form αs1-I CN, for the production of cheeses that can be sliced and shredded for an extended period of time, such as Mozzarella.

Such a chymosin also has quick early ripening so is useful for production of cheeses that have to be shredded or sliced as soon as possible (i.e. without prolonged storage).

Cheese made with a coagulant (chymosin) of the invention has a fast early development combined with increased storage stability. Therefore, such cheese can be shredded/sliced faster but also for a longer period of time without unacceptable losses or fouling of the equipment.

Any chymosin with an amino acid change at the corresponding position leads to an altered affinity of the alpha s1-casein for the S2 pocket of this chymosin and a change in the kinetics of the first cut in alpha s1-casein. For a person skilled in the art it will be clear how to change this amino acid in bovine chymosin or the equivalent amino acid in chymosins originating from other mammals, like a camel chymosin, to obtain a chymosin with altered digestion kinetics of the first cut in alpha s1-casein, and thereby will lead to a change in the textural characteristics of a cheese made with such variant.

A gene or cDNA coding for chymosin or pro-chymosin, for example a variant of the invention, may be cloned and over-expressed in a host organism. Well known host organisms that have been used for over-expression of enzymes include *Aspergillus*, *Kluyveromyces*, *Trichoderma*, *Escherichia coli*, *Pichia*, *Saccharomyces*, *Yarrowia*, *Neurospora*, *Bacillus*, *Fusarium*, *Hansenula*, *Chrysosporium* or *Candida*.

Currently, bovine chymosin is manufactured industrially using recombinant DNA technology, e.g. using filamentous fungi such as *Aspergillus* species, yeast strains, e.g. of *Klyuveromyces* species, or bacterial species, e.g. *E. coli*, as host organisms. Such recombinant microbial production strains are constructed and continuously improved using DNA technology as well as classical strain improvement measures directed towards optimising the expression and secretion of a heterologous protein.

In the invention, a chymosin variant may be provided in the form of pre-prochymosin, prochymosin or (mature) chymosin. A corresponding nucleic acid sequence may also be provided, i. e. a polynucleotide that encodes a pre-prochymosin, prochymosin or (mature) chymosin is provided. The sequence of such a pre-prochymosin-, prochymosin- or (mature) chymosin-encoding sequence may be optimized for expression in a desired host cellis.

The variants described herein are collectively comprised in the terms "a polypeptide according to the invention" or "a variant according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than about seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

A polypeptide of the invention may be in isolated form, such as substantially isolated form. By "isolated" polypeptide or protein is intended a polypeptide or protein removed from its native environment. For example, recombinantly produced polypeptides and proteins expressed in host cells are considered isolated for the purpose of the invention as are recombinant polypeptides which have been substantially purified by any suitable technique. A polypeptide variant according to the invention can be recovered and purified from recombinant cell cultures by methods known in the art.

Polypeptides of the present invention include products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also features biologically active fragments of the polypeptide variants according to the invention. Such fragments are considered to be encompassed within the term "a variant of the invention".

Biologically active fragments of a polypeptide variant of the invention include polypeptides comprising amino acid sequences sufficiently identical to or derived from the amino acid sequence of a variant protein of the invention which include fewer amino acids than the full length protein but which exhibit at least one biological activity of the corresponding full-length protein. Typically, biologically active fragments comprise a domain or motif with at least one activity of a variant protein of the invention. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

Typically, a protein fragment of the invention will comprise one or more of the substitutions defined herein.

The invention also features nucleic acid fragments which encode the above biologically active fragments (which biologically active fragments are themselves variants of the invention).

As set out above, the present invention provides polynucleotides encoding the variant polypeptides of the invention. The invention also relates to an isolated polynucleotide encoding at least one functional domain of a polypeptide variant of the invention. Typically, such a domain will comprise one or more of the substitutions described herein.

In one embodiment of the invention, the nucleic acid sequence according to the invention encodes a polypeptide, wherein the polypeptide is a variant comprising an amino acid sequence that has one or more truncation(s), and/or at least one substitution, deletion and/or insertion of an amino acid as compared to the parent asparaginase. Such a polypeptide will, however, typically comprise one or more of the substitutions described herein.

As used herein, the terms "gene" and "recombinant gene" refer to nucleic acid molecules which include an open reading frame encoding a variant as described herein. A gene may include coding sequences, non-coding sequences, introns and regulatory sequences. That is to say, a "gene", as used herein, may refer to an isolated nucleic acid molecule as defined herein. Accordingly, the term "gene", in the context of the present application, does not refer only to naturally-occurring sequences.

A nucleic acid molecule of the present invention can be generated using standard molecular biology techniques well known to those skilled in the art taken in combination with the sequence information provided herein.

For example, using standard synthetic techniques, the required nucleic acid molecule may be synthesized de novo. Such a synthetic process will typically be an automated process.

Alternatively, a nucleic acid molecule of the invention may be generated by use of site-directed mutagenesis of an existing nucleic acid molecule, for example a wild-type nucleic acid molecule. Site-directed mutagenesis may be carried out using a number of techniques well known to those skilled in the art.

In one such method, mentioned here merely by way of example, PCR is carried out on a plasmid template using oligonucleotide "primers" encoding the desired substitution. As the primers are the ends of newly-synthesized strands, should there be a mis-match during the first cycle in binding the template DNA strand, after that first round, the primer-based strand (containing the mutation) would be at equal concentration to the original template. After successive cycles, it would exponentially grow, and after 25, would outnumber the original, unmutated strand in the region of 8 million: 1, resulting in a nearly homogeneous solution of mutated amplified fragments. The template DNA may then be eliminated by enzymatic digestion with, for example using a restriction enzyme which cleaves only methylated DNA, such as Dpn1. The template, which is derived from an alkaline lysis plasmid preparation and therefore is methylated, is destroyed in this step, but the mutated plasmid is preserved because it was generated in vitro and is unmethylated as a result.

In such a method more than one mutation (encoding a substitution as described herein) may be introduced into a nucleic acid molecule in a single PCR reaction, for example by using one or more oligonucleotides, each comprising one or more mis-matches. Alternatively, more than one mutation may be introduced into a nucleic acid molecule by carrying out more than one PCR reaction, each reaction introducing one or more mutations, so that altered nucleic acids are introduced into the nucleic acid in a sequential, iterative fashion.

A nucleic acid of the invention can be generated using cDNA, mRNA or alternatively, genomic DNA, as a template and appropriate mis-matched oligonucleotide primers according to the site-directed mutagenesis technique described above. A nucleic acid molecule derived in this way can be cloned into an appropriate vector and characterized by DNA sequence analysis.

A nucleic acid sequence of the invention may comprise one or more deletions, i.e. gaps, in comparison to the parent chymosin. Such deletions/gaps may also be generated using site-directed mutagenesis using appropriate oligonucleotides. Techniques for generating such deletions are well known to those skilled in the art.

Furthermore, oligonucleotides corresponding to or hybridizable to nucleotide sequences according to the invention can be prepared by standard synthetic techniques, e.g., using an automated DNA synthesizer.

Also, complementary nucleic acid molecules are included in the present invention. A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a variant of the invention, or a biologically active fragment or domain thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules, such as for the preparation of nucleic acid molecules of the invention.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule of the invention.

The terms "homology" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Another aspect of the invention pertains to vectors, preferably expression vectors, containing a nucleic acid encoding a variant chymosin polypeptide of the invention.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g.

a chymosin variant of SEQ ID NO: 2 or SEQ ID: 4, for example a functional equivalent or fragment, or a fusion protein comprising one or more of such variants).

The recombinant expression vectors of the invention can be designed for expression of variant proteins of the invention in prokaryotic or eukaryotic cells. For example, a variant protein of the invention can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of chymosin in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a variant protein of the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in E. coli with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in E. coli and other bacteria. Representative examples of appropriate host include bacterial cells, such as E. coli, Streptomyces Salmonella typhimurium and certain Bacillus species; fungal cells such as Aspergillus species, for example A. niger, A. oryzae and A. nidulans, such as yeast such as Kluyveromyces, for example K. lactis and/or Puchia, for example P. pastoris; insect cells such as Drosophila S2 and Spodoptera Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promoters suitable for use in the present invention include the promoters disclosed in WO-A1-2004/074468, which are hereby incorporated by reference.

Transcription of the DNA encoding a variant of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

A variant of the invention may be expressed in form such that it may include additional heterologous functional regions, for example secretion signals. A variant of the invention may also comprise, for example, a region of additional amino acids, particularly charged amino acids, added to the N-terminus of the polypeptide for instance to improve stability and persistence in the host cell, during purification or during subsequent handling and storage. Also, peptide moieties may be added to a variant of the invention to facilitate purification, for example by the addition of histidine residues or a T7 tag.

The variants of the invention, such as proteins of the present invention or functional equivalents thereof, e.g., biologically active portions and fragments thereof, can be operatively linked to a non-variant polypeptide (e.g., heterologous amino acid sequences) to form fusion proteins. A "non-variant polypeptide" in this context refers to a polypeptide having an amino acid sequence corresponding to a protein which is not substantially homologous to a variant chymosin of the invention.

Within a fusion protein, the variant of the invention can correspond to a full length sequence or a biologically active fragment of a polypeptide of the invention. In a preferred embodiment, a fusion protein of the invention comprises at least two biologically active portions. Within the fusion protein, the term "operatively linked" is intended to indicate that the variant polypeptide and the non-variant polypeptide are fused in-frame to each other. The non-variant polypeptide can be fused to the N-terminus or C-terminus of the variant polypeptide.

Expression and secretion of a variant chymosin may be enhanced by expressing the variant in the form of a fusion protein. In this context, a nucleic acid sequence may encode for a fusion protein comprising pre-prochymosin, prochymosin or chymosin. More specifically, the fusion partner may be glucoamylase or a fragment thereof. In one embodiment the pre-prochymosin, prochymosin or chymosin, or a fusion protein thereof, is secreted over the host cell membrane.

For example, in one embodiment, the fusion protein is a fusion protein in which the variant sequence/s is/are fused to the C-terminus of the GST sequences. Such fusion proteins can facilitate the purification of a recombinant variant according to the invention. In another embodiment, the fusion protein is a variant of the invention containing a heterologous signal sequence at its N-terminus. In certain host cells (e.g., mammalian and yeast host cells), expression and/or secretion of a variant of the invention can be increased through use of a hetereologous signal sequence.

In another example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a variant of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence may direct secretion of the variant, such as from a eukaryotic host into which the expression vector is transformed, and the signal sequence may then be subsequently or concurrently cleaved. The variant of the invention may then be readily purified from the extracellular medium by known methods. Alternatively, the signal sequence can be linked to the variant of interest using a sequence, which facilitates purification, such as with a GST domain. Thus, for instance, the sequence encoding the variant of the invention may be fused to a marker sequence, such as a sequence encoding a peptide, which facilitates purification of the fused variant of the invention. In certain preferred embodiments of this aspect of the invention, the marker sequence is a hexahistidine peptide, such as the tag provided in a pQE vector (Qiagen, Inc.), among others, many of which are commercially available. As described in Gentz et al, Proc. Natl. Acad. Sci. USA 86:821-824 (1989), for instance, hexahistidine provides for convenient purification of the fusion protein. The HA tag is another peptide useful for purification which corresponds to an epitope derived of influenza hemaglutinin protein, which has been described by Wilson et al., Cell 37:767 (1984), for instance.

A fusion protein of the invention may be produced by standard recombinant DNA techniques. For example, DNA fragments coding for the different polypeptide sequences are ligated together in frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). A variant-encoding nucleic acid can be cloned into such an expression vector such that the fusion moiety is linked in-frame to the said variant.

The terms "functional equivalents" and "functional variants" are used interchangeably herein. Functional equivalents according to the invention are isolated DNA fragments that encode a polypeptide that exhibits a particular function of a variant as defined herein. Functional equivalents therefore also encompass biologically active fragments and are themselves encompassed within the term "a variant" of the invention.

Preferably, a functional equivalent of the invention comprises one or more of the substitutions described herein. However, a functional equivalent may comprise one or more modifications in addition to the substitutions described above.

Functional nucleic acid equivalents may typically contain silent mutations or mutations that do not alter the biological function of encoded polypeptide. Accordingly, the invention provides nucleic acid molecules encoding a variant chymosin protein that contains changes in amino acid residues that are not essential for a particular biological activity. Such variant proteins differ in amino acid sequence from the parent chymosin sequence from which they are derived yet retain at least one biological activity thereof, preferably they retain at least chymosin activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the reference amino acid sequence (for example that shown in SEQ ID NO: 2).

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

The skilled person will recognise that changes can be introduced by mutation into the nucleotide sequences according to the invention thereby leading to changes in the amino acid sequence of the resulting protein without substantially altering the function of such a protein.

Accordingly, a chymosin variant of the invention is preferably a protein which comprises an amino acid sequence at least about 60%, 65%, 70%, 75%, 80%, 85%, 90%, 95%, 96%, 97%, 98%, 99% or more homologous to the reference amino acid sequence, for example that shown in SEQ ID NO: 2, and typically also retains at least one functional activity of the reference polypeptide. Variants of the invention, for example functional equivalents of a protein according to the invention, can also be identified e.g. by screening combinatorial libraries of mutants, e.g. truncation mutants, of the protein of the invention for chymosin activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198: 1056; Ike et al. (1983) Nucleic Acid Res. 11:477).

In addition, libraries of fragments of the sequence encoding a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having chymosin activity include, inter alia, (1) in situ hybridization (e.g. FISH) to metaphase chromosomal spreads to provide precise chromosomal location of an chymosin-encoding gene as described in Verma et al., Human Chromosomes: a Manual of Basic Techniques, Pergamon Press, New York (1988); (2) Northern blot analysis for detecting expression of chymosin mRNA in specific tissues and/or cells; and (3) probes and primers that can be used as a diagnostic tool to analyse the presence of a nucleic acid hybridizable to such a probe or primer in a given biological (e.g. tissue) sample.

Variants of a given reference chymosin enzyme can be obtained by the following standard procedure:
Mutagenesis (error-prone, doped oligo, spiked oligo) or synthesis of variants
Transformation in, for example K. lactis
Cultivation of transformants, selection of transformants
Expression
Optional purification and concentration
Primary Screening
Identification of an improved variant (for example in relation to specific activity)

1. The invention thus relates to a method of producing a chymosin polypeptide variant, which method comprises:
a) selecting a polypeptide having chymosin activity;
b) substituting at least one amino acid residue corresponding to:
position 51 or 221 as defined with reference to SEQ ID NO: 2; and/or
a position within the S2 binding pocket as defined with reference to SEQ ID NO: 4;
c) optionally substituting one or more further amino acids as defined in b);
d) preparing the variant resulting from steps a)-c);
e) determining a property of the variant; and
f) selecting a variant having an altered property in comparison a reference polypeptide having chymosin activity, thereby to produce an chymosin polypeptide variant.

The invention relates to cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from yeasts, for example, K. lactis. Host cells also include, but are not limited to, mammalian cell lines such as CHO, VERO, BHK, HeLa, COS, MDCK, 293, 3T3, W138, and choroid plexus cell lines.

Examples of suitable bacterial host organisms are gram positive bacterial species such as Bacillaceae including *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium* and *Bacillus thuringiensis*, *Streptomyces* species such as *Streptomyces murinus*, lactic acid bacterial species including *Lactococcus* spp. such as *Lactococcus lactis*, *Lactobacillus* spp. including *Lactobacillus reuteri*, *Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Klyuveromyces* spp. including *Klyuveromyces lactis*.

Suitable host organisms among filamentous fungi include species of *Acremonium*, *Aspergillus*, *Fusarium*, *Humicola*, *Mucor*, *Myceliophtora*, *Neurospora*, *Penicillium*, *Thielavia*, *Tolypocladium* or *Trichoderma*, such as e. g. *Aspergillus aculeatus*, *Aspergillus awamori*, *Aspergillus foetidus*, *Aspergillus japonicus*, *Aspergillus oryzae*, *Aspergillus nidulans* or *Aspergillus niger*, including *Aspergillus* nigervar. *awamori*, *Fusarium bactridioides*, *Fusarium* cereals, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichiodes*, *Fusarium sulphureum*, *Fusarium torulosum*, *Fusarium trichothecioides*, *Fusarium venenatum*, *Humicola insolens*, *Humicola langinosa*, *Mucor miehei*, *Myceliophtora thermophila*, *Neurospora crassa*, *Penicillium chrysogenum*, *Penicillium camenbertii*, *Penicillium purpurogenum*, *Rhizomucor miehei*, *Thielavia terestris*, *Trichoderma harzianum*, *Trichoderma koningii*, *Trichoderma longibrachiatum*, *Trichoderma reesii* or *Trochoderma viride*.

A host cell can be chosen that modulates the expression of the inserted sequences, or modifies and processes the product encoded by the incorporated nucleic acid sequence in a specific, desired fashion. Such modifications (e.g., glycosylation) and processing (e.g., cleavage) of protein products may facilitate optimal functioning of the encoded protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

If desired, a stably transfected cell line can produce a variant according to the invention. A number of vectors suitable for stable transfection of mammalian cells are available to the public, methods for constructing such cell lines are also publicly known, e.g., in Ausubel et al. (supra).

The present invention further discloses a composition comprising the chymosin variants according to the invention. The composition may optionally comprise other ingredients such as e.g. other enzymes such as a pepsin. Such a composition may comprises the variant polypeptide of the invention or one obtainable by a method of the invention for identifying a variant chymosin.

In addition to the variant chymosin, and one or more additional enzymes, if present, a composition according to the invention may comprise additives that are conventionally used in rennets of animal origin such as e. g. NaCl.

The invention further relates to use of a variant polypeptide of the invention or a composition of the invention in the preparation of a cheese. Accordingly, the invention concerns a process for the production of a cheese, which method comprises comprising adding a milk clotting effective amount of a variant polypeptide or a composition of the invention to milk and carrying out appropriate further cheese manufacturing steps.

That is to say, the invention provides a process for preparing cheese, comprising, (i) supplementing milk with a chymosin variant or composition according to the invention, to effect coagulation of the milk, wherein a curd is obtained; and (ii) processing the curd into cheese.

In such a method of manufacturing cheese from milk, the milk may be cow's milk, camel's milk, buffalo milk, goat's milk, sheep's milk and a mixture of any such milk types. A polypeptide of the invention leads to a fast early development in ripening due to the rapid first cut in alpha s1-casein, but also leads to the possibility of prolonged storage of the cheese due to the high C/P value. Fast processibility requires high proteolytic activity and prolonged storage requires low proteolytic activity on the casein matrix. A polypeptide of the invention typically combines both of these properties Accordingly, the invention also encompasses use of a polypeptide or of a composition of the invention in the preparation of a cheese. Such use according to the invention may result in a cheese with improved processability, in particular in terms of shreddability/sliceability, and/or improved ripening and/or improved storage properties. These terms are described above.

Improved shreddability/sliceability in this context refers to a cheese which can be shredded/sliced over a longer period that a corresponding cheese made with a bovine or camel chymosin (for example those of SEQ ID NO: 2 or 4 respectively) or earlier in ripening that a cheese made with a camel chymosin (eg. that of SEQ ID NO: 4).

Improved storage in this context refers to a cheese which can be shredded/sliced over a longer period that a corresponding cheese made with a bovine or camel chymosin (for example those of SEQ ID NO: 2 or 4 respectively) or for longer during ripening that a cheese made with a bovine chymosin (eg. that of SEQ ID NO: 2).

Use of a polypeptide according to the invention thus leads to a coagulant for the production of cheese, in particular a young cheese for industrial use, that can stored for a prolonged period, but can also be processed early in the ripening, without extensive storage.

The invention relates to a cheese obtainable by such a process.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Materials & Methods
Medium Composition

YEP2D medium: 10 g/l yeast extract, 20 g/l bacto-peptone, 40 g/l glucose. pH was set to pH 6.7 with 4N NaOH. Medium was autoclaved for 30 minutes at 110° C.

YEP2D/MES medium: 10 g/l yeast extract, 20 g/l bacto-peptone, 40 g/l glucose, 20 g/l MES. pH was set to pH 6.7 with 4N NaOH. Medium was autoclaved for 30 minutes at 110° C.

YEP2D plates contain YEP2D medium with 1.8-2% agar. Medium was autoclaved for 30 minutes at 110° C. and poored in petridishes.

Buffer Composition

NaOH-MES buffer: prepare MES-buffer at pH 6.05 containing 50 g/kg MES and dilute 1 volume of 4 N NaOH with 7 volumes of the MES buffer.

Strains

GG799: This *Kluyveromyces lactis* strain is used as a wild-type strain. This strain is obtained from New England Biolabs, Ipswich, Mass., USA Molecular Biology Techniques Molecular biology techniques known to the skilled person were used (see: Sambrook & Russell, *Molecular Cloning: A Laboratory Manual*, 3rd Ed., CSHL Press, Cold Spring Harbor, N.Y., 2001). Examples of the general design of expression vectors for gene over expression, transformation, use of markers and selective media can be found in WO2007060247, WO2010102982 and U.S. Pat. No. 4,943,529 and references herein.

Clotting Activity (C)

A milk solution was prepared by adding 11 gram of Nilac milk powder (NIZO Food Science, Ede, the Netherlands) to 100 ml 4.5 mM CaCl2 (resulting pH 6.6-6.7). The solution was stirred for 30 minutes and kept in the dark for another 30 minutes. The milk is then ready and was used within half an hour. Subsequently, 5 ml milk solution was added to a test tube and pre-incubated for 5 minutes in a water bath of 32° C. The reaction was started by adding 100 µl enzyme to the milk solution. The milk clotting was followed visually in time. The moment coagulation starts is the point of clotting time. Different amounts of a diluted and purified Maxiren 1800 preparation (DSM Food-Specialties, Delft, the Netherlands) was used to obtain the reference curve for activity determination. 100 mg Maxiren 1800 was dissolved in 15 ml H2O, concentrated and washed out with H2O and 40 mM MES-NaOH, pH 5.7 using an Amicon Ultra centrifugal filter, 10 kDa. The final volume was adjusted to 5 ml. A series of clotting measurements at different concentrations was performed (set at 2, 4, 6, 8, 10, 12, 15 and 20 IMCU/ml in the Maxiren stock solution) and clotting time for each dilution was determined and the relation between the clotting time and the amount of units in the assay was determined. The clotting time found in the tested samples was calculated back to the IMCU activity of the original Maxiren stock solution, determined with this assay, and expressed in U/ml. This milk-clotting activity of the tested samples was used in the calculation of the C/P (see below).

General Proteolytic Activity (P)

Proteolytic activity was estimated using casein sodium salt from bovine milk (Sigma, C8654) as substrate. The reaction mix (750 µl) contained: 730 µl substrate (0.5% casein in 33 mM MES, pH 5.8) and 20 µl sample to be tested. The reaction mix was incubated for 120 min at 32° C. and the reaction was terminated by addition of 250 µl 12% (w/w) TCA with vigorous stirring on a vortex mixer. To determine OD280 (t=0 min) the reaction was stopped immediately after start. The OD280 of the supernatants was measured after centrifugation at 12,000 rpm for 10 min. The difference (deltaOD) between OD280 (t=120 min) and OD280 (t=0 min) was calculated and is a measurement of the proteolytic activity at pH5.8 in the tested samples. The proteolytic activity (P) was calculated back to the original sample concentration by multiplying with a factor 50 and used for the calculation of the C/P (see below).

Texture Profile Analysis (TPA)

For the texture analyser a 25 mm thick slab of cheese was cut off with a cheese knife, the thickness was reduced to 20 mm by the aid of an electric meat slicer to ensure the slab thickness was homogeneous. From the cheese slab cylinders of 16 mm width were cut with a cheese borer. Samples were stored overnight refrigerated at ~4° C. in a ziplock plastic bag. A square compression plate (7×7 cm) was attached to a TA.HD.plus Texture Analyser (Stable Micro Systems). Cheese samples were compressed for 70% in tenfold at a compression rate of 1 mm/s.

Measurements were recorded with the program Exponent. With this program the peak positive force, peak positive distance, peak force, positive area and negative area of the two peak of each measurement was determined. With Excel the distance at the start of the second peak was determined. From this data the fracturability (peak force 1 (F), firmness (peak positive force 1 (H), cohesiveness (positive area 2/positive area 1 (A2/A1), gumminess (firmness*cohesiveness), and adhesiveness (negative area 1 (A3)) could be calculated (FIG. 1). Data was entered in SPSS for statistical analysis with one-way Anova with a post-hoc Tukey test (when there was homogeneity of variances) or a post-hoc Games-Howell test (in case the assumption of homogeneity of variances was violated) to detect significant differences between cheeses.

Alpha-Casein Hydrolysis and Analysis

A suspension of 20 mg/ml alpha casein from bovine milk (C6780, Sigma) in 50 mM sodium acetate buffer pH 5.5 containing 0.02% sodium azide was prepared and divided into 1 ml portions. The suspension was pre-incubated for at least 12 hours at 11° C. under continuous shaking at 1400 rpm (Eppendorf thermomixer). Each coagulant was diluted in 50 mM sodium acetate buffer pH 5.5 to a final concentration of 4 IMCU/ml and kept overnight at 4° C. Subsequently, 100 µl of the cold coagulant stock solution was added to 1 ml of pre incubated substrate. Incubation was at 11° C. or 30° C. under continuous shaking at 1400 rpm. As a control, 50 mM sodium acetate buffer pH 5.5 instead of the coagulant stock was added. Samples of 60 µl were taken after different time points and immediately incubated for 10 minutes at 75° C. to inactivate the coagulant. Inactivated samples were stored on ice.

Subsequently the same volume of buffer containing 0.1 M 1,3-bis[tris(hydroxymethyl)-methylamino]propane (Bis-Tris), 8 M Urea, 0.3% 2-mercaptoethanol (ME) and 1.3% trisodium citrate dehydrate (pH7) was added to the sample and incubated for 10 minutes at 50° C. This mixture was cooled down to room temperature before a 5 µl sample was taken and added to 60 µl dilution buffer containing 62 mM Tris and 0.7% ME (pH 7.6). An amount of 25 µl Nupage LDS Sample Buffer (Life Technologies) was added. Finally a volume of 10 µl Nupage sample reducing agent (Life Technologies) was added to achieve a final volume of 100 µl, which was incubated at 70° C. for 5-10 minutes before analysis using SDS-PAGE. An amount of 4 µl sample was applied on 10% Bis-Tris SDS-PAGE gel (Life Technologies) and electrophoresis was performed in MES buffer (Life technologies) for 15 minutes at 50V and continued for 45 minutes at 200V. The gel was removed from the frame after electrophoresis and stained at room temperature with Instant Blue (Expedeon) for at least one hour and subsequently destained for several hours. The gel was imaged and photographed. The stained proteins were quantified using the software TotalLab TL 100, 1 D analysis.

Example 1: DNA Constructs and Transformation

Synthetic DNA constructs were designed to start with a XhoI restriction site, encoding amino acids L and E, followed in frame with DNA encoding a kex-protease cleavage site with amino acids K and R, followed by in frame genes encoding variants of bovine pro-chymosin B starting with amino acids A, E, I and T, ending with a PacI restriction site just after the stop codon. As an example, a DNA fragment encoding the wild type bovine pro-chymosin B sequence is listed as SEQ ID NO: 1 and a DNA fragment encoding the wild type camel pro-chymosin sequence is listed as SEQ ID NO: 3. Codon usage was adapted according to the method described in patent application US090286280. All variants were designed in a similar fashion and cloned as XhoI PacI fragments in vector pKLAC1 (New England Biolabs, Ipswich, Mass., USA).

The resulting open reading frames start with the leader sequence of the *K. lactis* Mating Factor alpha and progresses over the kex processing site to the pro-chymosin B variants. Amino acid changes that were introduced into the bovine chymosin variants are depicted in Table 1. Position of the change is indicated in comparison with the mature bovine chymosin B sequence (SEQ ID NO: 2). Some amino acid positions are changed into various different amino acids, like position K221 (variant #5-7) or position A51 (variant #1 and 103). Some other variants have multiple changes introduced into the amino acid sequence of the chymosin protein, like variants #71, 74, 98, 103 and 110. A wild-type gene encoding the unchanged bovine pro-chymosin protein was also used in gene cloning and transformation and was later used to compare with enzymes made with the variant genes.

Transformation and strain selection were performed by electroporation and selection on acetamide containing plates essentially as described in WO2007/060247. The plasmids were linearized by digestion with SacII and transformed to *Kluyveromyces lactis* strain GG799 by electroporation. Of each construct six transformants were tested for chymosin production using shake flask fermentations, and the best producing transformant was selected for further analysis Example 2: Cultivation, Activation and Concentration The *Kluyveromyces lactis* strains harbouring a mutant bovine pro-chymosin gene were placed on YEP2D agar plate and grown for 48 hours at 30° C. A pre-culture in 20 ml of YEP2D medium in 100 ml Erlenmeyer flasks was inoculated with the yeast cells taken from the plates. The cultures were grown for 24 hours in an incubator shaker at 30° C. and 250 rpm. The amount of pre-culture for inoculation of new 500 ml Erlenmeyer flasks with 100 ml YEP2D/MES medium was calculated to give a final OD600=0.01. These main cultures were grown for 65 hours in an incubator shaker at 30° C. and 250 rpm. For strain conservation 2 ml of pre-culture were centrifuged (4000 rpm and 10 min), cell pellet was suspended in 0.7 ml 70% glycerol and stored at −60° C.

Pro-chymosin was converted (activated) into mature chymosin by a pH step as described below. 35 g of the broth of the main culture after 65 hours cultivation was centrifuged at 8000 rpm for 15 minutes (10° C.) and 17 ml of the supernatant was used for activation of pro-chymosin. Activation was done by adding diluted hydrochloric acid (1 N) in small aliquots (typically by adding the 1N HCl in 50-200 µl volume) to the sample ensuring good mixing to avoid local pH effects. The pH of the sample was adjusted to 2.35-2.40 (pH of grown culture was 6.7-6.9). After 30-90 minutes incubation at 30° C. the pH was adjusted to 6.05±0.05 with NaOH-MES buffer.

Activated chymosin samples were 20 times concentrated and the medium components were washed out with 40 mM MES-NaOH, pH 5.7 using diafiltration. For this an Amicon Ultra centrifugal filter, 10 kDa was used. The starting volume of the activated sample was 20 ml and the volume of the final concentrated sample was 1 ml. The samples were formulated by addition of 1 ml glycerol. The extent of the final concentration was therefore 10-fold. These samples were used for all examples described later. To analyze the chymosin expression level and to check the extent of the activation the samples were loaded on a 4-12% gradient SDS-PAGE (NuPAGE 4-12% Bis-Tris Gel, Invitrogen). The following molecular weight marker was used: SeeBlue Plus2 Pre-Stained Standard, Invitrogen (188, 98, 62, 49, 38, 28, 17, 14, 7, 3 kDa). Activation of pro-chymosin seemed to be complete in all variant chymosins.

TABLE 1

Amino acid changes introduced in the protein sequence of bovine chymosin B.
Amino acids aredepicted according to the single letter annotation.
Numbering is set out with reference to SEQ ID NO: 2

| Variant # | Amino acid change | | | | | | | |
|---|---|---|---|---|---|---|---|---|
| 1 | A51V | | | | | | | |
| 5 | K221L | | | | | | | |
| 6 | K221M | | | | | | | |
| 7 | K221V | | | | | | | |
| 62 | V223Q | | | | | | | |
| 71 | A51V | K221V | | | | | | |
| 74 | A51V | K221M | | | | | | |
| 98 | A51V | K221V | S135T | A126G | S273Y | Q240E | | |
| 103 | A51I | K221T | | | | | | |
| 110 | A51V | K221V | N50D | N144H | N160D | S201D | Q242E | M267E | Q280E |

Example 3: Activity Determination

The specificity of chymosin (C/P) is an important parameter for the functional properties of the enzyme in the cheese making process. The specificity of an individual chymosin sample can be calculated by dividing the milk clotting activity (C) by the general proteolytic activity (P). In the experiments described here the relative C/P is being used. For this the C/P calculated for a specific variant is divided by the C/P calculated for Maxiren 1800. The relative C/P for Maxiren 1800 is set at 1.0.

As can be seen in Table 2, when variants with mutations at position A51 and/or K221 were tested this way, all show a higher relative C/P ratio than Maxiren. Variants 1-7 all have mutations at position A51 and/or K221 of the mature calf chymosin B. Although the single mutants 1, 5, 6, and 7 give a relatively modest increase in C/P, surprisingly the combination of mutations at positions A51 and K221 (variants 71, 74, 98, 103 and 110) give a synergistic effect on the increase in C/P. The relative C/P measured in these samples is much higher than that of any of the coagulants described by Kappeler et al. The coagulant with the highest relative C/P in their study is a recombinant camel chymosin with a C/P value of 7, relative to bovine chymosin. This camel chymosin is currently sold under the brand name Chymax M (Chr. Hansen).

TABLE 2

Relative C/P calculated for different chymosin variants

| Variant # | Rel. C/P (average) |
|---|---|
| 1 | 5.3 |
| 5 | 1.2 |
| 6 | 1.2 |
| 7 | 4.1 |
| 62 | 1.6 |
| 71 | 16.8 |
| 74 | 12.2 |
| 98 | 15.1 |
| 103 | 23.1 |
| 110 | 23.1 |

Example 4: Production of Miniature Mozzarella Cheese Using Chymosin Variants

Miniature Mozzarella was produced at a 1 liter scale. Full fat, non homogenised milk was used (Demeter, organic milk obtained in a local health food store) and brought to a temperature of 34° C. As starter culture DelvoTEC TS80M was used at a level of 2 units per 1000 liters of milk (obtained from DSM Food Specialties, Delft, the Netherlands). The milk was preripened for 60 minutes followed by addition of rennet (60 IMCU/L). The milk was left to coagulate for 60 minutes after which the coagulum was cut by specially designed wire cutters. The curd/whey mixture was allowed a 10 minute healing time after which the cooking step started. The temperature was increased to 41° C. within half an hour whilst stirred intermittently. Upon reaching the aimed for cooking temperature, the pH was checked regularly and when a pH of 6.2 was reached in the curd/whey mixture, the curd was drained and the cheddaring phase started. During this phase the curd slab was halved and neatly stacked and every 15 minutes the stack was turned. When a pH of 5.1-5.2 was reached, the curd was milled and salted at a rate of 3% (w/w). Following a 2 minute mellowing time, 400 mls of hot water, 80° C., was added and the curds was stretched and moulded manually for 3 minutes. Afterwards the small balls of Mozzarella were placed in ice and cooled. Once cooled, the Mozzarella balls were dried using tissue paper and vacuum-sealed and ripened at 4° C.

TABLE 3

Total nitrogen (TN), soluble nitrogen (SN) and amino nitrogen (AN) determined in 2 weeks Mozzarella cheeses made with selected variants. Controls are cheeses made with Maxiren and Chymax M

| Rennet used | TN (%) | SN (%) | AN (%) | SN/TN | AN/TN |
|---|---|---|---|---|---|
| Chymax M | 3.54 | 0.09 | 0.025 | 2.5 | 0.7 |
| Maxiren | 3.56 | 0.17 | 0.02 | 4.8 | 0.6 |
| #71 | 3.57 | 0.185 | 0.02 | 5.2 | 0.6 |
| #74 | 3.53 | 0.15 | 0.02 | 4.2 | 0.6 |
| #103 | 3.55 | 0.165 | 0.025 | 4.6 | 0.7 |

Results of this experiment are shown in Table 3. Nitrogen content of the different cheeses was determined by Qlip (the Netherlands) using standard procedures. Surprisingly, after 2 weeks of ripening the soluble nitrogen (SN) content of the Mozzarella cheeses made with variants 71, 74 and 103 is similar to the SN measured with Maxiren, although the C/P of these variants is much higher. Chymax M, which has a C/P of 7 (Kappeler et al), shows a lower SN value.

Example 5: Production of Cheddar Cheese Using Chymosin Variants

It has been suggested by Bansal et al. (Int. Dairy J. 19, 510-517 (2009)) that recombinant camel chymosin can be used to make Cheddar cheese with a firmer texture. It was suggested that these effects are due to the lower proteolytic activity and higher C/P of camel chymosin compared to calf chymosin. Since the calf chymosin variants described here have an even higher relative C/P, we wished to investigate these coagulants in Cheddar cheese making.

Cheddar cheese was produced at the pilot plant of the DSM Biotechnology center (Delft, the Netherlands) using variant 74 and compared to control Cheddar made with recombinant calf chymosin (Maxiren 600: DSM-Food specialties) or recombinant camel chymosin (Chymax M: Chr. Hansen). Cheddar cheeses were manufactured in the pilot plant using three 200 liter cheese vats. The cheese vats were filled with 175 liter of full fat, pasteurised bovine milk and tempered to 32° C. Starter culture was added (DelvoTEC LL50A) at a level of 4 units per 1000 liters of cheese milk. Calcium chloride was also added to each vat (50 mls of a 33% solution). After one hour of pre-ripening, rennet was added to the cheese vat and mixed well before being left to stand for the coagulation to take place. It was found that the IMCU dosage of variant 74 could be reduced by 20% compared to Maxiren to obtain a similar coagulation of the cheese milk. Therefore 47 IMCU/l were added for Maxiren 600 and both 37.6 IMCU/l for Chymax M and #74. Once a quite firm gel was formed, the coagulum was cut using knives. For 10 minutes the gel was cut using an incremental speed (from 0 to 11). After this time, the cooking step was initiated and in 30 minutes, the temperature of the curd/whey mixture was increased to 38° C. whilst continuous stirring the mixture at speed 16. Once this temperature was reached, the curd/whey mixture was stirred until a pH was reached of 6.2 upon which the curds were drained. This was followed by the cheddaring step in which the formed slabs of curd were turned every 15 minutes and stacked after the second turning. Once the pH in the curd slabs had dropped to 5.3, the slabs were milled and dry salted (645 grams of salt were added to the milled curd of 175 liters of full fat milk). The salted, milled curds were left to mellow for 15 minutes before being transferred to rectangular cheese moulds. The cheeses were pressed overnight at 4 bar. After pressing, the cheeses were vacuum sealed and ripened at 11° C.

Example 6: Texture Profile Analysis of Cheddar Cheese

Figure 2:
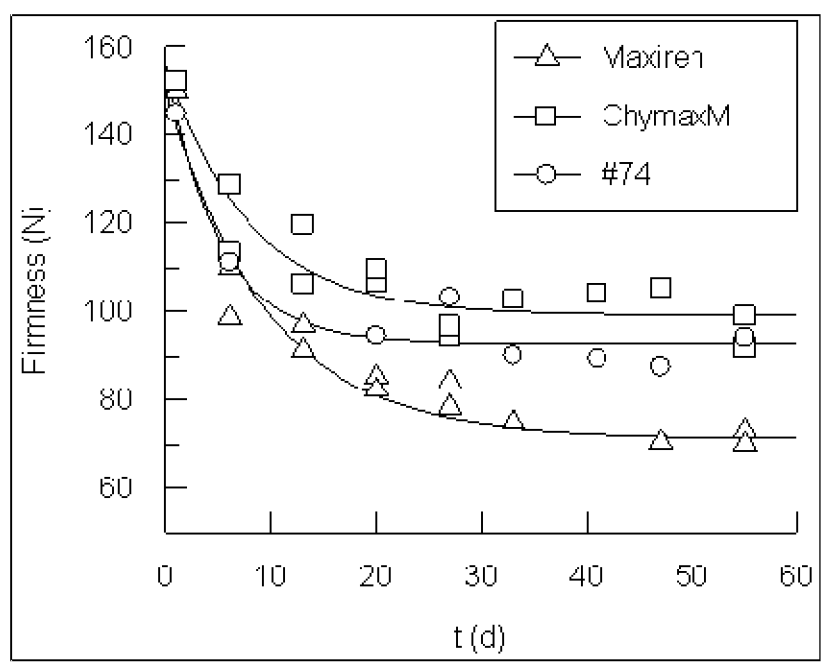
FIG. 2 sets out the results of the measurement of firmness in Cheddar cheeses made with Variant #74, Maxiren and Chymax M coagulants. Average values for individual cheeses are shown.

The cheeses produced in Example 5 were used for texture profile analysis (TPA) during 12 weeks of ripening. For every time point a piece of cheese of suitable size was cut from the block and resealed. Results of the firmness analysis using TPA analysis of the cheeses are described in the Material & Methods section and the results are represented in FIG. 2.

Surprisingly, at early time points (1-2 weeks) the development of the firmness of the cheeses made with variant #74 chymosin is not similar to the cheeses made with Chymax M, but more familiar to the cheeses made with Maxiren. This was not expected since variant #74 has a relative C/P that is even higher than the relative C/P of Chymax M. Also the related measurement of gumminess is lower than with Chymax M-made cheese and more similar to Maxiren-made cheese. In the first few weeks no significant differences were found in other textural parameters, like adhesiveness, between all cheeses.

Surprisingly, after the first few weeks softening in the #74 cheese stops and firmness stays constant at a level similar to Chymax M-made cheese.

Besides firmness, also the adhesiveness of the cheeses was followed in time. Results are depicted in Table 4. During the first 5 weeks of ripening differences in adhesiveness between the different cheeses are small and fall within the experimental error. However, after 5 weeks of ripening the adhesiveness of the Maxiren-made cheese became more prominent, while Chymax M-made and #74-made cheeses did not show increased adhesiveness.

TPA thus shows that cheese made with #74 chymosin performs like Maxiren in early cheese ripening, but more like Chymax M in later time points.

TABLE 4

Adhesiveness measured using TPA on cheeses made with #74, Maxiren and Chymax M as coagulant and ripened for the indicated time in days

| t (d) | 74 | Maxiren | ChymaxM |
|---|---|---|---|
| 6 | −0.09 | −0.23 | −0.26 |
| 13 | −0.08 | −0.18 | −0.13 |
| 20 | −0.23 | −0.15 | 0.00 |
| 27 | −0.24 | −0.37 | −0.04 |
| 33 | −0.22 | −0.40 | −0.08 |
| 41 | −0.33 | −1.51 | −0.14 |
| 47 | −0.30 | −1.09 | −0.19 |
| 55 | −0.35 | −0.99 | −0.48 |

Example 7: Shredding of Cheddar Cheese

The Cheddar cheese produced in example 5 was cut into slabs of approximately 250 grams with a cheese knife at different stages of ripening. Each slab was shredded using a cheese grater (Santos; version 2) provided with a standard stainless steel disc with 3 mm holes fixed to a motor of 1500 turns per minute. An amount of 100 gram grated cheese was applied on the top of pre-weighted sieve with apertures of 4.00 mm (Endecotts Ltd.) supported by a pre-weighted reservoir. The grated cheese was distributed over the surface of the sieve by hand. The stack of the cheese filled sieve with reservoir was put on the vibration plate of a sieve shaker (Octagon D 200; Endecotts Ltd.) and clamped firmly. Sieving was performed at an amplitude level of 6 for 6 minutes with an intermittent vibration of 0.4 minutes at 8 degrees Celsius. Subsequently, the sieve and reservoir were weighted separately. The amount of cheese in the reservoir was defined as fines and calculated after correction of the weight of the empty reservoir. The percentage of fines was calculated taking the applied grated cheese into account as presented in table 5.

TABLE 5

Percentage (w/w) fines (<4 mm) upon shredding of Cheddar cheeses made with different coagulants and ripened for the indicated time period

| Week | #74 | Maxiren | Chymax M |
|---|---|---|---|
| 1 | 10.82% | 8.61% | 16.83% |
| 2 | 7.76% | 4.75% | 14.42% |
| 3 | 5.84% | 2.99% | 8.00% |
| 4 | 7.14% | 4.10% | 7.69% |
| 6 | 6.48% | 3.81% | 7.65% |

As can be seen in table 5, the amount of fines in Cheddar cheese made with Chymax M is unacceptably high at early time points in the ripening. The amount of fines produced from the Cheddar cheese made with #74 is more familiar to the cheese made with Maxiren. This result was unexpected since Variant #74 has a very high C/P and therefore was expected to react more similar to Chymax M during ripening. However, the amount of fines upon shredding of young cheeses was clearly reduced, and this variant has therefore an advantage over cheese produced with Chymax M.

The variant chymosins described here have therefore an advantage compared to Chymax M type of coagulant for shredding of very young cheeses and an advantage compared to Maxiren type of coagulants for more aged cheeses in terms of a reduction in adhesiveness.

Example 8: Proteolytic Activity of Chymosin Variants on Alpha-Casein

We tested the activity of the different variants of chymosin on the degradation of alpha-casein in vitro, in order to determine the proteolytic specificity of the different variants and compare to Maxiren and Chymax M. Alpha s1-casein is known to be the first target of chymosin during cheese ripening and is therefore a relevant substrate to test the activity of different coagulants.

The procedure to perform the alpha-casein hydrolysis and quantification of the hydrolytic products is described in the Materials and methods section. The pixel intensity of the different (degraded) casein bands is summarized in tables 6 and 7. "αs1 CN" indicates the intact, non-hydrolysed αs1-casein band. "αs1-I CN" indicates the band migrating directly beneath the αs1-casein band which has been described as the first hydrolysis product of αs1-casein where chymosin has digested the F23F24 bond. The C-terminal hydrolytic product of this is called αs1-I casein or αs1-CN (f24-199). Separation and location of the αs1 and αs1-I bands have also been described in literature and can be established and quantified with different techniques, apart from the method described here. See for example Bansal et al (2009) International dairy Journal 19, 510-517, and Borsting et al. (2012) Dairy Sci. & Technol. 92, 593-612. "Small" indicates the intensity of all smaller degradation products still visible by SDS-PAGE as described in Materials & Methods. It is understood that more severe degradation of alpha-casein will lead to even smaller peptides that are not detectable anymore by SDS-PAGE.

Results presented in Table 6 are obtained from an incubation of alpha-casein with different chymosin variants at 11° C., while the results presented in Table 7 are obtained by incubation at 30° C.

TABLE 6

Hydrolysis of alpha-s1 casein with different chymosin variants. Incubation was performed at 11° C. for the indicated time. Intensity of different proteins was determined by scanning of stained bands after separation by SDS-PAGE.

| | 6 hours Volume (×E6) | | | | 24 hours Volume (×E6) | | | |
|---|---|---|---|---|---|---|---|---|
| Coagulant | αs1 CN | αs1-1 CN | small | αs1-1 CN/ αs1 CN | αs1 CN | αs1-1 CN | small | αs1-1 CN/ αs1 CN |
| no | 37.4 | 0.0 | 0.0 | 0.0 | 34.7 | 0.0 | 0.0 | 0.0 |
| Chymax M | 27.3 | 12.8 | 0.0 | 0.5 | 12.5 | 16.2 | 11.0 | 1.3 |
| Maxiren | 11.4 | 21.2 | 0.0 | 1.9 | 1.6 | 15.9 | 6.7 | 9.7 |
| 1 | 20.5 | 18.8 | 0.0 | 0.9 | 5.8 | 23.6 | 0.0 | 4.1 |
| 6 | 18.1 | 18.9 | 0.0 | 1.0 | 5.1 | 22.2 | 4.3 | 4.3 |
| 7 | 10.7 | 22.8 | 0.0 | 2.1 | 2.8 | 18.2 | 10.5 | 6.4 |
| 71 | 8.8 | 25.4 | 0.0 | 2.9 | 2.5 | 24.6 | 0.0 | 9.8 |
| 74 | 20.9 | 19.8 | 0.0 | 0.9 | 6.3 | 24.7 | 0.0 | 3.9 |

TABLE 7

Hydrolysis of alpha-s1 casein with different chymosin variants. Incubation was performed at 30° C. for the indicated time. Intensity of different proteins was determined by scanning of stained bands after separation by SDS-PAGE

| | 16 hours Volume (×E6) | | |
|---|---|---|---|
| Coagulant | αs1 CN | αs1-I CN | small |
| no | 37.5 | 0.0 | 0.0 |
| Chymax M | 0.0 | 4.3 | 9.0 |
| Maxiren | 0.9 | 0.6 | 8.1 |
| 71 | 1.6 | 19.7 | 2.4 |
| 74 | 1.8 | 18.6 | 5.1 |
| 98 | 1.5 | 19.6 | 1.4 |
| 103 | 1.4 | 20.3 | 1.3 |
| 110 | 3.0 | 22.6 | 1.4 |

From these experiments it is very clear that the all variants that contain changes in amino acids at position A51 and/or K221 of the mature calf chymosin B, show a clear hydrolysis of the first cut in alpha-s1-casein, leading to a rapid formation of fragment alpha-s1-I casein. This rapid first cut is similar to the situation with wild-type calf chymosin (Maxiren) and contrasts with the action of camel chymosin (Chymax M) that shows a slow first cut in alpha-s1 casein. After this first cut there is a very slow further hydrolysis of this fragment with the variants containing changes in amino acids at position A51 and/or K221 of the mature calf chymosin B; the alpha-s1-I casein band stays largely intact when incubation is extended to 24 hours (Table 6), or when the temperature is increased to 30° C. (Table 7). This contrasts the hydrolysis profile of both Maxiren and Chymax M that show further degradation of the alpha-s1-I fragment.

These results and the results described in previous Examples suggest that the first cut in alpha-s1-casein is required for the rapid development of the cheese matrix leading to improved shredding in young cheeses. This property of the variant chymosin molecules as described herein contrasts with other high C/P coagulants like Chymax M, described earlier. The high C/P of the variant coagulants lead to a very slow further degradation of alpha-s1-I casein and this has as effect that the cheese does not become too sticky upon longer ripening. Shredding will therefore still be possible after prolonged storage without severe production losses due to clumping and fouling.

Example 9: Proteolytic Activity of a Chymosin Variant Mutated at Position V223

We further investigated the effect of variant 62 on the proteolytic degradation of alpha s1-casein. The experiment was performed in a similar method as described above in example 7, by incubation of the substrate with the different coagulants at 11° C. and analysis of different time samples. Results are presented in Table 8.

From these results it is clear that variant 62 surprisingly shows a similar behaviour as Chymax M concerning the activity on alpha s1-casein. In contrast to the wild type calf chymosin (Maxiren) variant 62 shows slow hydrolysis of the first cut in alpha s1-casein, and therefore slow accumulation of alpha s1-I casein. It can be seen therefore that an amino acid change at position V223 of the calf chymosin sequence leads to a clear change in the hydrolysis kinetics at this first cut in alpha s1-casein. This result indicates that this amino acid position is important in modulating the kinetics of this first cut and thereby for the early development in the cheese.

TABLE 8

Hydrolysis of alpha-s1 casein with different chymosin variants. Incubation was performed at 11° C. for the indicated time. Intensity of different proteins was determined by scanning of stained bands after separation by SDS-PAGE.

| | 6 hours Volume (×E6) | | | 24 hours Volume (×E6) | | |
|---|---|---|---|---|---|---|
| Coagulant | αs1 CN | αs1-I CN | small | αs1 CN | αs1-I CN | small |
| no | 37.4 | 0.0 | 0.0 | 34.7 | 0.0 | 0.0 |
| Chymax M | 27.3 | 12.8 | 0.0 | 12.5 | 16.2 | 11.0 |
| Maxiren | 11.4 | 21.2 | 0.0 | 1.6 | 15.9 | 6.7 |
| 62 | 26.7 | 12.9 | 0.0 | 13.4 | 19.9 | 4.1 |

Example 10: Sensory Analysis of Cheddar Cheese

After 12 weeks of ripening samples were taken from the Cheddar cheeses produced in Example 5 and used for sensory analysis. Prior to the sensory panel session, the Cheddar cheeses were cut in cubes. Hereafter the samples were placed in an expanded polystyrene box to prevent them from warming up. The products were given in a polystyrene sample holder with a watch glass on top for easy shaking of the products to produce enough head space for assessing the odour of the cheddar cheese. The Quantitative Descriptive Analysis (QDA) method was used for these experiments. The products were evaluated twice by 13 trained cheese panelists. As the aim of the experiment was to measure the differences between the products, the products were given at random in order to avoid sequence effects. The products were given one-by-one to the panelists. As the aim of the experiment was to measure the differences between the products, the products were given at random in order to avoid sequence effects. The data were analysed using SenPaq software (QI-statistics). Statistical significant product differences were computed by means of ANOVA (Analysis of Variance) for each attribute. If a statistical significant product difference occurred, a Multiple Comparison Analysis was computed to investigate which products differed from each other. Only attributes that were scored significantly different are described below.

For the flavour attributes, the Cheddar made with Chymax M showed the least intense flavour. Also salty flavour was significantly lower than in the cheeses made with Maxiren and variant #74. No significant differences were found in other flavour attributes. Therefore the cheeses made with variant #74 differ from Chymax M-made cheese mainly with respect to flavour intensity.

For the mouth-feel attributes the cheese made with Maxiren was significantly different from the Chymax M and #74-made cheeses. The Maxiren cheese was less hard then the other two samples. Both stickiness and rubbery attributes were scored lower in #74 and Chymax M cheese than in Maxiren cheese. With respect to mouth-feel only the attribute fatty was significantly higher in #74-made cheese than in Chymax M-made cheese. In all other aspects #74-cheese resembled the Chymax M cheese.

For the odour attributes no significant differences were perceived between the different cheeses.

These results show that the texture development in #74 cheese resembles Chymax M cheese while the flavour development resembles Maxiren cheese.

Example 11: Production of Mozzarella Cheese

Full fat Mozzarella was produced in 275 liter cheese vats. In total 6 cheese vats were produced: 3 replicates Full fat Mozzarella with Maxiren®600 and 3 replicates with #74 coagulant.

Fresh cow milk was standardized to the desired fat-protein level; pasteurized for 15 seconds at 73° C. and cooled to 34° C. After filling the cheese vats a *S. thermophilus* culture was added to the cheese milk: 60 gram TS-10C (DSM Food Specialties). The cheese milk was acidified for 45 minutes before the coagulant was added. To 3 cheese vats 19.0 ml Maxiren®600; 582 IMCU/ml was added. In order to obtain the same coagulation time 18.8 ml #74; 500 IMCU/ml was added to 3 other cheese vats. After 35 minutes setting the curd was cut and stirred gently for 20 minutes. The temperature of the curd-whey mixture was slowly heated to 41° C. by means of hot water in the jacket of the cheese vat during 30 minutes. After gradually drawing whey from the cheese vat, the pH of the curds dropped to pH 5.25 under continuous stirring of the curds.

The cruds were salted with 1.8 kilo of dry sodium-chloride and transferred to the cooker-stretcher, filled with water of 68° C. The cheese blocks were directly from the cooker-stretcher placed in a brine-bath of 5% sodium-chloride; pH 5.3 and 1° C.

After 1 hour cooling down in the brine-bath the cheeses were vacuum packed and stored at 7° C. until analysis.

Results of the proximate analysis of all cheeses are shown in Table 9. The moisture values are relatively high and the pH values are relatively low for these type of cheeses.

TABLE 9

Analysis of all Mozzarella cheeses.

| Cheese | Rennet | % Moisture | % Fat | pH | % Salt |
|---|---|---|---|---|---|
| Full-fat 1 | Maxiren | 50.99 | 23.50 | 5.10 | 1.08 |
| Full-fat 2 | Maxiren | 52.23 | 23.00 | 5.05 | 1.06 |
| Full-fat 3 | Maxiren | 51.83 | 23.25 | 5.12 | 1.14 |
| Full-fat 4 | #74 | 50.81 | 23.00 | 5.12 | 1.12 |
| Full-fat 5 | #74 | 50.79 | 23.50 | 5.12 | 1.02 |
| Full-fat 6 | #74 | 51.34 | 23.75 | 5.15 | 1.16 |

Example 12: Shredding of Mozzarella Cheese

Approximately 500 g samples of each cheese were shredded at one and three weeks of age with a retail shredder (Salad Shooter, National Presto Industries, Eau Claire, Wis.). While shredding, 7.5 g of Solka-Floc (International Fiber Corporation, North Tonawanda, N.Y.) was added to prevent shreds from sticking together. The shreds were passed through a set of US Standard Testing Sieves (Fisher Scientific, Suwanee, Ga.), while continuously shaking (W. S. Tyler, Mentor, Ohio) for one minute. The amount of cheese retained in each sieve was determined by weight, and the result express as a percentage of the total cheese shredded.

The distribution of shred size for all cheeses is shown in Table 10. The values shown for the Maxiren and #74 cheeses are averages of the three replicates. The shred size distribution for the one-week old Maxiren, and #74 cheeses are similar. The shred size distribution for the three week old Maxiren and #74 cheeses are shifted toward the larges sieve sizes. This is due to the softer texture of the older cheeses that resulted in more balling of the shreds. This effect is much less prominent in the cheese made with #74 coagulant. Therefore, shreddability of older cheeses is improved when a coagulant with a higher C/P is used, compared to cheeses made with wild-type bovine chymosin.

TABLE 10

Average shred size distribution after ripening Mozzarella cheese for 1 and 3 weeks. Percentage of total cheese weight collected on the various sieves is depicted.

| Ripening time | Rennet | Sieve size (mm) | | | | | | | |
|---|---|---|---|---|---|---|---|---|---|
| | | 25.0 | 19.0 | 12.5 | 9.5 | 8.0 | 6.3 | 4.0 | none |
| 1 week | Maxiren | 0.0 | 0.0 | 0.1 | 5.2 | 9.2 | 18.8 | 45.4 | 21.4 |
| 1 week | #74 | 0.0 | 0.0 | 0.1 | 3.0 | 7.5 | 20.2 | 46.8 | 22.4 |
| 3 weeks | Maxiren | 26.6 | 29.7 | 20.1 | 8.8 | 4.2 | 4.3 | 4.8 | 1.5 |
| 3 weeks | #74 | 2.3 | 10.4 | 25.8 | 16.2 | 10.4 | 10.2 | 16.7 | 7.9 |

Example 13: Melting and Stretching Behavior of Mozzarella Cheese

The fork stretch test was used to evaluate the ability of the cheese to stretch after cooking on a pizza. A frozen pizza crust twelve inches in diameter was coated with 114 g pizza sauce, and 284 g of shredded cheese (Example 12) was evenly distributed over the pizza. It was then cooked at 250° C. for six minutes in an Impinger oven. The pizza was allowed to cool to 65° C. A fork was inserted approximately 2 cm into the cheese and lifted above the pizza. The length of the cheese when the stand broke was recorded as the stretch length. Each pizza was tested at three different places and the average stretch length for all three replicates of the Mozzarella cheeses is shown in Table 11. Average stretch length of the #74 cheeses was clearly improved compared to Maxiren cheeses at all ripening ages, but especially different in older cheeses. Apparently a coagulant with a high C/P ratio leads to a cheese with better stretchability in ripened cheeses.

TABLE 11

Average stretch length (cm) of cheeses of different age after melting on a pizza

| Ripening time | Rennet | |
|---|---|---|
| | Maxiren | #74 |
| 1 week | 52 | 59 |
| 3 weeks | 38 | 43 |
| 9 weeks | 4 | 30 |

Example 14: Proteolytic Activity of Camel Chymosin Variants

A number of camel chymosin variants were produced essentially as described in Example 1, but in this case based on the sequence of the mature camel chymosin sequence (SEQ ID NO: 4). Some amino acid positions of this protein were changed into various different amino acids. The list of changes that gave relevant changes in the proteolytic behavior of the camel chymosin is described in Table 12. The genes for the different camel chymosin variants were cloned and overexpressed in K. lactis essentially as described in Example 1 and 2. The isolated enzymes were used for further analysis of the C/P and the activity on alpha-s1 casein. C/P of the camel chymosin variants was determined as described in the Materials & Methods section and Example 3. The determination of the activity of the camel chymosin variants on alpha-s1 casein and quantification of the results was done as described in the Material & Methods section.

TABLE 12

Amino acid changes introduced in the protein sequence of camel chymosin. Amino acids are depicted according to the single letter annotation. Numbering is set out with reference to SEQ ID NO: 4

| Variant # | Amino acid change |
|---|---|
| 136 | F223C |
| 137 | F223D |
| 138 | F223E |
| 139 | F223L |
| 140 | F223M |
| 141 | F223N |
| 142 | F223Q |
| 143 | F223V |
| 144 | F223Y |
| 145 | F223I |
| 146 | Q288G |
| 147 | Q288H |
| 148 | Q288N |
| 149 | Q288R |
| 150 | Q288S |
| 151 | D290A |
| 152 | D290G |
| 153 | D290L |
| 154 | D290M |
| 155 | D290Q |
| 156 | D290S |
| 157 | D290T |
| 158 | L295F |
| 159 | L295I |
| 160 | L295K |
| 161 | L295M |
| 162 | L295R |
| 163 | L295T |
| 164 | L295Y |
| 165 | L295W |
| 166 | I297T |
| 167 | I297V |

A number of camel chymosin variants showed a significantly increased proteolysis of the F23F24 bond in αs1-casein compared to wild-type camel chymosin. Results of this experiment are depicted in Table 13.

TABLE 13

Hydrolysis of alpha-s1 casein with different camel chymosin variants. Incubation was performed at 11° C. for the indicated time. Intensity of different proteins was determined by scanning of stained bands after separation by SDS-PAGE.

| | 6 hours Volume (×E6) | | | 24 hours Volume (×E6) | | |
|---|---|---|---|---|---|---|
| Variant # | αs1 CN | αs1-I CN | (αSN1-1)/ (αSN1) | αs1 CN | αs1-I CN | (αSN1-1)/ (αSN1) |
| 136 | 28.6 | 20.6 | 0.7 | 10.6 | 20.3 | 1.9 |
| 137 | 31.4 | 22.6 | 0.7 | 11.0 | 25.5 | 2.3 |
| 138 | 32.9 | 20.0 | 0.6 | 17.4 | 24.7 | 1.4 |
| 139 | 21.0 | 25.9 | 1.2 | 2.9 | 12.4 | 4.3 |

TABLE 13-continued

Hydrolysis of alpha-s1 casein with different camel chymosin variants. Incubation was performed at 11° C. for the indicated time. Intensity of different proteins was determined by scanning of stained bands after separation by SDS-PAGE.

|  | 6 hours Volume (×E6) | | | 24 hours Volume (×E6) | | |
|---|---|---|---|---|---|---|
| Variant # | αs1 CN | αs1-I CN | (αSN1-1)/ (αSN1) | αs1 CN | αs1-I CN | (αSN1-1)/ (αSN1) |
| 140 | 32.2 | 23.4 | 0.7 | 11.4 | 22.7 | 2.0 |
| 141 | 35.7 | 25.7 | 0.7 | 12.7 | 24.9 | 2.0 |
| 142 | 37.2 | 25.5 | 0.7 | 10.2 | 17.5 | 1.7 |
| 143 | 23.6 | 26.2 | 1.1 | 4.1 | 10.0 | 2.4 |
| 144 | 31.2 | 30.5 | 1.0 | 8.4 | 28.2 | 3.3 |
| 145 | 15.7 | 19.1 | 1.2 | 2.8 | 11.7 | 4.1 |
| 146 | 23.8 | 21.7 | 0.9 | 12.3 | 28.5 | 2.3 |
| 147 | 21.5 | 22.8 | 1.1 | 7.0 | 23.5 | 3.3 |
| 148 | 28.3 | 17.4 | 0.6 | 20.3 | 26.2 | 1.3 |
| 149 | 22.2 | 21.6 | 1.0 | 6.7 | 22.5 | 3.3 |
| 150 | 28.7 | 18.3 | 0.6 | 17.2 | 23.1 | 1.3 |
| 151 | 23.1 | 22.9 | 1.0 | 13.1 | 32.2 | 2.5 |
| 152 | 25.1 | 21.8 | 0.9 | 9.7 | 33.3 | 3.4 |
| 153 | 23.6 | 23.5 | 1.0 | 7.1 | 34.9 | 4.9 |
| 154 | 25.2 | 26.9 | 1.1 | 8.3 | 37.7 | 4.6 |
| 155 | 30.2 | 20.3 | 0.7 | 13.5 | 33.6 | 2.5 |
| 156 | 31.5 | 17.0 | 0.5 | 17.1 | 31.6 | 1.9 |
| 157 | 30.7 | 17.6 | 0.6 | 13.6 | 23.8 | 1.7 |
| 158 | 26.3 | 19.5 | 0.7 | 9.8 | 22.2 | 2.3 |
| 159 | 29.5 | 17.0 | 0.6 | 11.1 | 19.7 | 1.8 |
| 160 | 29.5 | 18.1 | 0.6 | 12.0 | 24.9 | 2.1 |
| 161 | 31.5 | 19.6 | 0.6 | 11.0 | 22.3 | 2.0 |
| 162 | 30.9 | 16.5 | 0.5 | 16.7 | 31.0 | 1.9 |
| 163 | 27.9 | 14.8 | 0.5 | 11.4 | 17.9 | 1.6 |
| 164 | 24.9 | 15.9 | 0.6 | 14.9 | 26.6 | 1.8 |
| 165 | 21.2 | 30.9 | 1.5 | 5.7 | 37.8 | 6.7 |
| 166 | 21.0 | 18.0 | 0.9 | 4.2 | 13.3 | 3.1 |
| 167 | 27.3 | 20.2 | 0.7 | 8.0 | 22.9 | 2.9 |
| Chymax M average | 35.2 | 18.1 | 0.5 | 17.3 | 21.3 | 1.2 |
| Maxiren average | 15.8 | 26.3 | 1.7 | 4.0 | 25.2 | 6.3 |

TABLE 14

Relative C/P calculated for different camel chymosin variants

| Variant # | Rel. C/P |
|---|---|
| 137 | 6.3 |
| 139 | 7.7 |
| 143 | >10 |
| 144 | >10 |
| 145 | >10 |
| 146 | 5.1 |
| 147 | 8.0 |
| 149 | 5.9 |
| 151 | 8.3 |
| 152 | >10 |
| 153 | 9.0 |
| 154 | 9.3 |
| 155 | 5.9 |
| 165 | >10 |
| 166 | 3.1 |
| 167 | 8.1 |

The C/P of the different camel chymosin variants was determined and the results are depicted in Table 14. The C/P of all camel variants tested was still clearly higher than the C/P of calf chymosin From this experiments it becomes clear that the camel chymosin can be specifically engineered in order to obtain increased hydrolytic activity on the F23F24 bond of αs1-casein without a serious reduction of the C/P of the enzyme. Such camel chymosin variants may therefore be suitable for the production of cheeses which can be processed already early in ripening, in contrast to wild type camel chymosin (see Example 7). Shredding of cheeses made with such chymosins will therefore both be possible early in ripening and after prolonged storage without severe production losses due to clumping and fouling.

The invention claimed is:

1. A polypeptide having chymosin activity and comprising an amino acid sequence that has at least 90% sequence identity to SEQ ID NO:4, comprises at least one substitution modification relative to SEQ ID NO:4 selected from the group consisting of Q288H, and Q288R, and is capable of hydrolysing bovine alpha s1-casein at position F23F24 so as to form αs1-I CN (f24-199) more rapidly than the polypeptide of SEQ ID NO:4.

2. The polypeptide of claim 1, wherein the hydrolysis of bovine alpha s1-casein at position F23F24 forming αs1-I CN (f24-199) by the polypeptide is at least 1.25 times more rapid than the hydrolysis of bovine alpha s1-casein at position F23F24 forming αs1-I CN (f24-199) by the polypeptide of SEQ ID NO:4.

3. The polypeptide of claim 1, wherein the polypeptide has a C/P ratio greater than the C/P ratio of the polypeptide of SEQ ID NO:2.

4. The polypeptide of claim 1, further comprising at least one substitution modification relative to SEQ ID NO:4, located at position 219, 223, 290, 295 or 297 when aligned with SEQ ID NO:4.

5. The polypeptide of claim 1, which shares at least about 95% sequence identity with the polypeptide according to SEQ ID NO: 4.

6. The polypeptide of claim 1, further comprising at least one substitution modification selected from the group consisting of F223C, F223D, F223E, F223L, F223M, F223N, F223Q, F223V, F223Y, F223I, D290A, D290G, D290L, D290M, D290Q, D290S, D290T, L295F, L295I, L295K, L295M, L295R, L295T, L295Y, L295W, I297T, and I297V.

7. The polypeptide of claim 1, wherein the chymosin is produced recombinantly.

8. A composition comprising the polypeptide claim 1.

9. The polypeptide of claim 1, wherein a cheese prepared with the polypeptide:
   demonstrates earlier ripening than a cheese prepared with the polypeptide of SEQ ID NO:4; and/or
   can be shredded and/or sliced over a longer period than a cheese prepared with the polypeptide of SEQ ID NO:4.

10. The polypeptide of claim 3, wherein a cheese prepared with the polypeptide:
    demonstrates earlier ripening than a cheese prepared with the polypeptide of SEQ ID NO:4; and/or
    can be shredded and/or sliced over a longer period than a cheese prepared with the polypeptide of SEQ ID NO:4.

11. A nucleic acid encoding the polypeptide of claim 1.

12. A nucleic acid construct comprising the nucleic acid sequence of the nucleic acid of claim 11 operably linked to one or more control sequences capable of directing expression of a chymosin in a suitable expression host.

13. A recombinant expression vector comprising the nucleic acid construct of claim 12.

14. A recombinant host cell comprising the expression vector of claim 13.

15. A method for producing a chymosin comprising cultivating the host cell of claim 14 under conditions conducive to production of the chymosin and recovering the chymosin.

16. A process for production of a cheese, which method comprises adding a milk clotting effective amount of the polypeptide of claim 1 to milk and carrying out appropriate further cheese manufacturing.

* * * * *

SEQUENCE LISTING

<160> NUMBER OF SEQ ID NOS: 5

<210> SEQ ID NO 1
<211> LENGTH: 1119
<212> TYPE: DNA
<213> ORGANISM: Bos taurus

<400> SEQUENCE: 1

```
ctcgagaaaa gagctgaaat caccagaatt ccattgtaca agggtaagtc tttgagaaag      60
gctttgaagg aacacggtct attggaagat ttcttacaaa agcaacagta cggtatttct     120
tccaagtact ccggtttcgg tgaagttgcc tccgtcccat tgaccaacta tctggactct     180
caatatttcg gtaagatcta cttgggtact ccacctcaag agttcaccgt ccttttcgac     240
actggttctt ctgatttctg ggttccatcc atctactgta agtccaatgc ttgtaagaac     300
catcaaagat tgacccaag aaagtcttcc actttccaaa acttgggtaa gccattatcc     360
attcactatg gtactggttc catgcaaggt atcttgggtt acgacactgt tactgtttcc     420
aacattgttg acattcaaca aaccgtcggt ttgtccactc aagagcctgg cgatgttttc     480
acctacgctg aatttgatgg tatttttgggt atggcttacc catctttggc ttctgaatac     540
tccatccctg tctttgacaa catgatgaac cgtcacttgg ttgctcaaga tttattctcc     600
```

-continued

```
gtttacatgg acagaaacgg tcaagaatcc atgttgactt taggtgccat tgatccatct    660
tactacactg ttctctaca ctgggttcca gttaccgtcc aacaatactg gcaattcacc     720
gttgactccg tcaccatctc cggtgttgtt gttgcttgtg aaggtggttg ccaagctatc    780
ttggacaccg gtacttccaa gttggtcggt ccatcttctg atatcttgaa cattcaacaa    840
gccattggtg ccactcaaaa ccagtacggt gaattcgata ttgactgtga caacttgtct    900
tacatgccaa ctgttgtctt tgaaatcaat ggtaagatgt acccattaac cccatctgct    960
tacacttctc aagaccaagg tttctgtact tctggtttcc aatctgaaaa ccattctcaa   1020
aaatggatct tgggtgatgt cttcatcaga gagtactact ccgtctttga ccgtgccaac   1080
aacttggttg gtttggccaa ggccatctaa gttaattaa                          1119
```

<210> SEQ ID NO 2
<211> LENGTH: 323
<212> TYPE: PRT
<213> ORGANISM: Bos taurus

<400> SEQUENCE: 2

```
Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30

Phe Asp Thr Gly Ser Ser Asp Phe Trp Val Pro Ser Ile Tyr Cys Lys
        35                  40                  45

Ser Asn Ala Cys Lys Asn His Gln Arg Phe Asp Pro Arg Lys Ser Ser
    50                  55                  60

Thr Phe Gln Asn Leu Gly Lys Pro Leu Ser Ile His Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
        115                 120                 125

Ser Leu Ala Ser Glu Tyr Ser Ile Pro Val Phe Asp Asn Met Met Asn
    130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

Phe Thr Val Asp Ser Val Thr Ile Ser Gly Val Val Val Ala Cys Glu
        195                 200                 205

Gly Gly Cys Gln Ala Ile Leu Asp Thr Gly Thr Ser Lys Leu Val Gly
    210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
            260                 265                 270

Ser Ala Tyr Thr Ser Gln Asp Gln Gly Phe Cys Thr Ser Gly Phe Gln
        275                 280                 285
```

```
Ser Glu Asn His Ser Gln Lys Trp Ile Leu Gly Asp Val Phe Ile Arg
    290                 295                 300
Glu Tyr Tyr Ser Val Phe Asp Arg Ala Asn Asn Leu Val Gly Leu Ala
305                 310                 315                 320
Lys Ala Ile
```

<210> SEQ ID NO 3
<211> LENGTH: 1095
<212> TYPE: DNA
<213> ORGANISM: Camelus dromedarius

<400> SEQUENCE: 3

```
tctggtatca ccagaattcc attgcacaag ggtaagactt tgagaaaggc tttgaaggaa      60
agaggtttgt tggaagattt cttgcaaaga caacaatacg ctgtctcttc caaatactct    120
tctttgggta aggttgccag agaaccattg acttcttact tggactctca atacttcggt    180
aagatctaca ttggtactcc acctcaagaa ttcaccgttg tctttgacac tggttcttct    240
gatttatggg ttccatctat ctactgtaaa tccaatgtct gtaagaacca ccacagattt    300
gacccaagaa agtcttccac tttcagaaac ttgggtaagc cattatccat tcactacggt    360
actggttcca tggaaggttt cttgggttac gataccgtta ccgtttccaa catcgttgac    420
ccaaaccaaa ccgtcggtct atccactgaa caaccaggtg aagttttcac ctactctgaa    480
ttcgatggta tcttaggttt ggcttaccca tctttggcct ccgaatactc cgtcccagtt    540
ttcgacaaca tgatggacag acatttggtt gctcgtgatt gttctccgt ctacatggac    600
agaaacggtc aaggttccat gttgactttg ggtgccattg acccatctta ctacactggt    660
tctttgcact gggttccagt caccttgcaa caatactggc aattcaccgt tgactctgtc    720
accatcaacg tgttgctgt tgcttgtgtc ggtggttgtc aagctatttt ggataccggt    780
acttctgtct tgttcggtcc atcttctgat atcttgaaga tccaaatggc cattggtgct    840
actgaaaacc gttatggtga atttgatgtc aactgtggta acttgagatc catgccaacc    900
gttgttttcg aaatcaacgg tcgtgactac ccattgtctc catctgctta cacttccaag    960
gaccaaggtt tctgtacctc tggtttccaa ggtgacaaca actctgaatt atggatcttg   1020
ggtgatgttt tcatcagaga atactactcc gtcttcgaca gagctaacaa cagagtcggt   1080
ttagctaagg ctatt                                                    1095
```

<210> SEQ ID NO 4
<211> LENGTH: 323
<212> TYPE: PRT
<213> ORGANISM: Camelus dromedarius

<400> SEQUENCE: 4

```
Gly Lys Val Ala Arg Glu Pro Leu Thr Ser Tyr Leu Asp Ser Gln Tyr
1               5                   10                  15
Phe Gly Lys Ile Tyr Ile Gly Thr Pro Pro Gln Glu Phe Thr Val Val
            20                  25                  30
Phe Asp Thr Gly Ser Ser Asp Leu Trp Val Pro Ser Ile Tyr Cys Lys
        35                  40                  45
Ser Asn Val Cys Lys Asn His His Arg Phe Asp Pro Arg Lys Ser Ser
    50                  55                  60
Thr Phe Arg Asn Leu Gly Lys Pro Leu Ser Ile His Tyr Gly Thr Gly
65                  70                  75                  80
Ser Met Glu Gly Phe Leu Gly Tyr Asp Thr Val Thr Val Ser Asn Ile
                85                  90                  95
```

-continued

Val Asp Pro Asn Gln Thr Val Gly Leu Ser Thr Glu Gln Pro Gly Glu
            100                 105                 110

Val Phe Thr Tyr Ser Glu Phe Asp Gly Ile Leu Gly Leu Ala Tyr Pro
        115                 120                 125

Ser Leu Ala Ser Glu Tyr Ser Val Pro Val Phe Asp Asn Met Met Asp
130                 135                 140

Arg His Leu Val Ala Arg Asp Leu Phe Ser Val Tyr Met Asp Arg Asn
145                 150                 155                 160

Gly Gln Gly Ser Met Leu Thr Leu Gly Ala Ile Asp Pro Ser Tyr Tyr
                165                 170                 175

Thr Gly Ser Leu His Trp Val Pro Val Thr Leu Gln Gln Tyr Trp Gln
            180                 185                 190

Phe Thr Val Asp Ser Val Thr Ile Asn Gly Val Ala Val Ala Cys Val
        195                 200                 205

Gly Gly Cys Gln Ala Ile Leu Asp Thr Gly Thr Ser Val Leu Phe Gly
210                 215                 220

Pro Ser Ser Asp Ile Leu Lys Ile Gln Met Ala Ile Gly Ala Thr Glu
225                 230                 235                 240

Asn Arg Tyr Gly Glu Phe Asp Val Asn Cys Gly Asn Leu Arg Ser Met
                245                 250                 255

Pro Thr Val Val Phe Glu Ile Asn Gly Arg Asp Tyr Pro Leu Ser Pro
            260                 265                 270

Ser Ala Tyr Thr Ser Lys Asp Gln Gly Phe Cys Thr Ser Gly Phe Gln
        275                 280                 285

Gly Asp Asn Asn Ser Glu Leu Trp Ile Leu Gly Asp Val Phe Ile Arg
290                 295                 300

Glu Tyr Tyr Ser Val Phe Asp Arg Ala Asn Asn Arg Val Gly Leu Ala
305                 310                 315                 320

Lys Ala Ile

<210> SEQ ID NO 5
<211> LENGTH: 199
<212> TYPE: PRT
<213> ORGANISM: Bos taurus

<400> SEQUENCE: 5

Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
50                  55                  60

Ile Ser Ser Ser Glu Glu Ile Val Pro Asn Ser Val Glu Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
130                 135                 140

```
Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
                180                 185                 190

Lys Thr Thr Met Pro Leu Trp
            195
```